(12) United States Patent
Grabowska et al.

(10) Patent No.: US 9,932,371 B2
(45) Date of Patent: Apr. 3, 2018

(54) PROMISCUOUS HPV16-DERIVED T HELPER EPITOPES FOR IMMUNOTHERAPY

(71) Applicant: Deutsches Krebsforschungszentrum Stiftung des Öffentlichen Rechts, Heidelberg (DE)

(72) Inventors: Agnieszka Grabowska, Stuttgart (DE); Angelika Riemer, Heidelberg (DE)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 0 days.

(21) Appl. No.: 15/104,165

(22) PCT Filed: Dec. 1, 2014

(86) PCT No.: PCT/EP2014/076048
§ 371 (c)(1),
(2) Date: Jun. 13, 2016

(87) PCT Pub. No.: WO2015/086354
PCT Pub. Date: Jun. 18, 2015

(65) Prior Publication Data
US 2016/0311861 A1 Oct. 27, 2016

(30) Foreign Application Priority Data
Dec. 12, 2013 (EP) ..................... 13196923

(51) Int. Cl.
| | | |
|---|---|---|
| *C07K 7/00* | (2006.01) | |
| *C07K 9/00* | (2006.01) | |
| *C07K 14/025* | (2006.01) | |
| *A61K 39/12* | (2006.01) | |
| *A61K 38/04* | (2006.01) | |
| *C07K 14/005* | (2006.01) | |
| *C07K 7/08* | (2006.01) | |
| *C12N 7/00* | (2006.01) | |
| *A61K 38/00* | (2006.01) | |
| *A61K 39/00* | (2006.01) | |

(52) U.S. Cl.
CPC ............ *C07K 14/005* (2013.01); *A61K 39/12* (2013.01); *C07K 7/08* (2013.01); *C12N 7/00* (2013.01); *A61K 38/00* (2013.01); *A61K 39/00* (2013.01); *A61K 2039/525* (2013.01); *A61K 2039/57* (2013.01); *A61K 2039/572* (2013.01); *C07K 2319/74* (2013.01); *C12N 2710/20022* (2013.01); *C12N 2710/20034* (2013.01); *C12N 2710/20051* (2013.01)

(58) Field of Classification Search
None
See application file for complete search history.

(56) References Cited

U.S. PATENT DOCUMENTS

| | | | |
|---|---|---|---|
| 7,026,443 B1 | 4/2006 | Sette et al. | |
| 8,252,893 B2 * | 8/2012 | Kim ................. | A61K 39/12 530/300 |
| 2010/0196353 A1 * | 8/2010 | Van Der Burg ....... | A61K 39/12 514/1.1 |

FOREIGN PATENT DOCUMENTS

| | | |
|---|---|---|
| EP | 1 288 292 A1 | 3/2003 |
| WO | WO 2004/031211 A2 | 4/2004 |
| WO | WO 2010/027973 A1 | 3/2010 |

OTHER PUBLICATIONS van den Hende et al. Skin reactions to human papillomavirus (HPV) 16 specific antigens intradermally injected in healthy subjects and patients with cervical neoplasia. Int J Cancer. Jul. 1, 2008;123(1):146-52.*
Database UniProt, Jul. 5, 2004, XP002723613, Accession No. UNIPROT:Q77AB6.
Grabowska, Agnieszka et al., "Abstract 1267: Identification of HPV-derived CD4+ T-helper epitopes for improving therapeutic anti-HPV vaccine potency," *Cancer Research*, Apr. 15, 2013, 73(8-Suppl 1):1-2.
Gupta, Shishir K. et al., "In silico accelerated identification of structurally conserved CD8+ and CD4+ T-cell epitopes in high-risk HPV types," *Infection, Genetics and Evolution*, 2012, 12:1513-1518.
Liao, Shu-jie et al., "HPV16 E5 Peptide Vaccine in Treatment of Cervical Cancer In Vitro and In Vivo," *J Huazhong Univ Sci Technol*, 2013, 33(5):735-742.
Wang, Xuelian et al., "A novel CD4 T-cell epitope described from one of the cervical cancer patients vaccinated with HPV 16 or 18 E7-pulsed dendritic cells," *Cancer Immunol Immunother*, 2009, 58:301-308.
Xu, Minzhen et al., "Ii-Key/HPV16 E7 hybrid peptide immunotherapy for HPV16+ cancers," *Vaccine*, 2009, 27:4641-4647.

* cited by examiner

*Primary Examiner* — Nianxiang Zou
(74) *Attorney, Agent, or Firm* — Saliwanchik, Lloyd & Eisenschenk

(57) ABSTRACT

The present invention relates to novel amino acid sequences of peptides derived from HPV16 that are able to bind to MHC complexes of class II, and elicit an immune response. The present invention further relates to pharmaceutical products, such as vaccines and T-cells, based on said epitopes.

7 Claims, 8 Drawing Sheets

PROMISCUOUS HPV16-DERIVED T HELPER EPITOPES FOR IMMUNOTHERAPY

CROSS REFERENCE TO A RELATED APPLICATION

Figure 1:
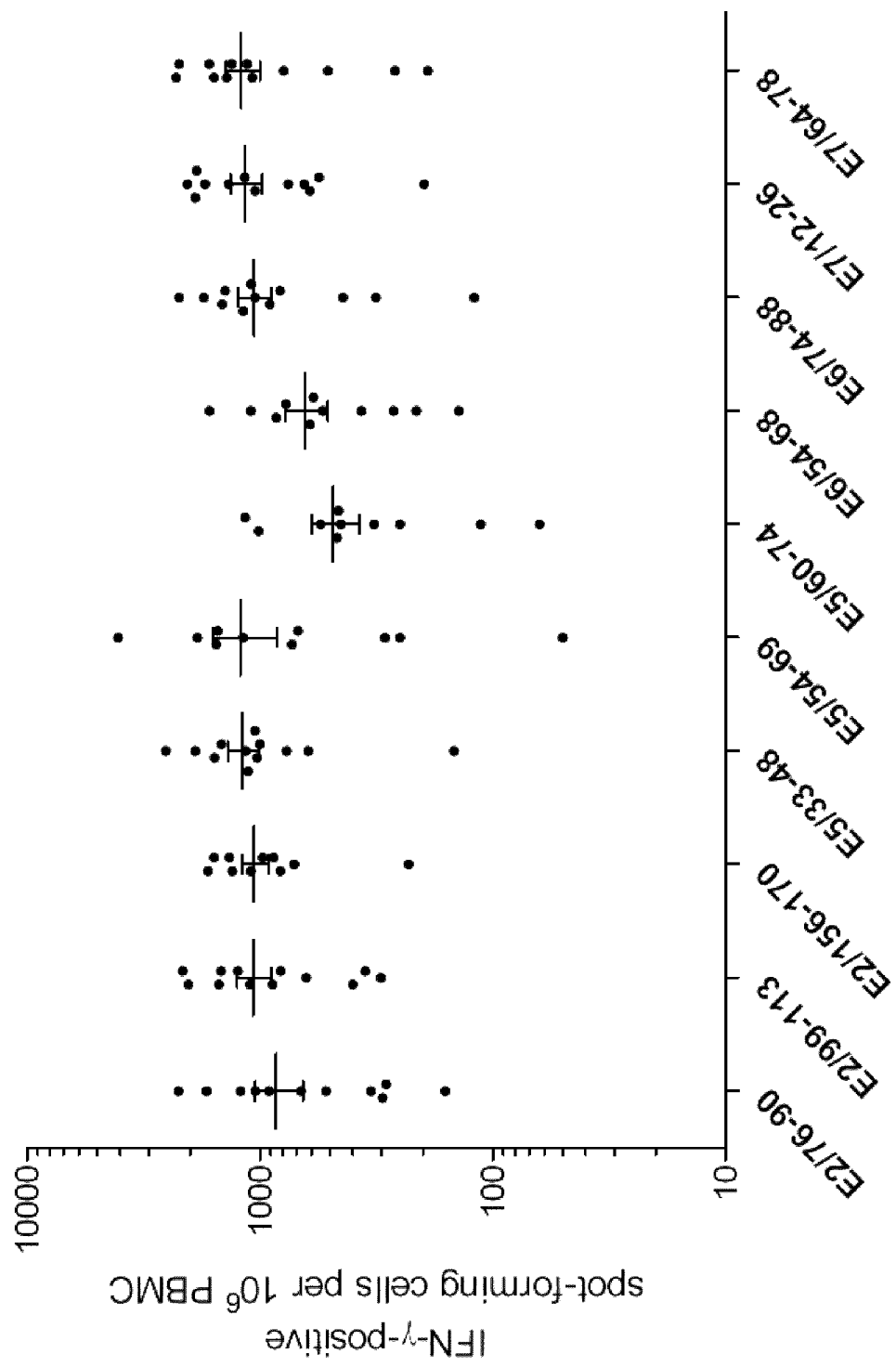

This application is a National Stage Application of International Application Number PCT/EP2014/076048, filed Dec. 1, 2014; which claims priority to European Application No. 13196923.0, filed Dec. 12, 2013; which are incorporated herein by reference in their entirety.

The present invention relates to novel amino acid sequences of peptides derived from HPV16 that are able to bind to MHC complexes of class II, and elicit an immune response. The present invention further relates to pharmaceutical products, such as vaccines and T-cells, based on said epitopes.

BACKGROUND OF THE INVENTION

Cervical carcinoma and several other human papillomavirus (HPV)-induced malignancies are a global public health problem, thus novel treatment modalities are urgently needed. Immunotherapy is an attractive option for treatment of infection and (pre)malignant lesions. However, previous approaches—focusing on the induction of cytotoxic CD8+ T cells—have as yet not yielded substantial clinical successes. Since CD4+ T cells have been shown to be crucial for the induction and maintenance of cytotoxic CD8+ T cell responses, and more recently to be also important for direct anti-tumor immunity, HLA class II-restricted epitopes are intensively investigated to improve the efficacy of peptide-based HPV immunotherapy.

High-risk types of human papillomavirus (HPV) are associated with several malignant diseases, including cervical carcinoma, other anogenital tumors, and oropharyngeal carcinomas (zur Hausen H. 1987. Papillomaviruses in human cancer. *Appl Pathol* 5: 19-24; Bosch F X, et al. The causal relation between human papillomavirus and cervical cancer. *J Clin Pathol* 55: 244-65; Gillison M L, et al. 2012. Human papillomavirus and diseases of the upper airway: head and neck cancer and respiratory papillomatosis. *Vaccine* 30 Suppl 5: F34-541-3). Natural history studies indicate that nearly every sexually active individual will acquire at least one high-risk HPV infection during their lifetime (Baseman J G, Koutsky L A. 2005. The epidemiology of human papillomavirus infections. *J Clin Virol* 32 Suppl 1: S16-24, Schiffman M, Castle P E, Jeronimo J, Rodriguez A C). Fortunately, the majority of HPV infections are eradicated by the host immune system within 1-2 years of acquisition (Woodman C B, Collins S I, Young L S. 2007. The natural history of cervical HPV infection: unresolved issues. *Nat Rev Cancer* 7: 11-22, Rodriguez A C, et al. 2010. Longitudinal study of human papillomavirus persistence and cervical intraepithelial neoplasia grade 2/3: critical role of duration of infection. *J Natl Cancer Inst* 102: 315-24), and only <1% of infected people develop HPV-mediated cancers (Evander M, et al. 1995. Human papillomavirus infection is transient in young women: a population-based cohort study. *J Infect Dis* 171: 1026-30, Koutsky L. 1997. Epidemiology of genital human papillomavirus infection. *Am J Med* 102: 3-8). Why some individuals clear the viral infection, while others do not, is still incompletely understood. Accumulating data suggest that both cytotoxic CD8+ T cell (CTL) and CD4+ T helper (Th) cell responses play a pivotal role in the control and clearance of HPV infection (Stanley M A. 2001. Immunobiology of papillomavirus infections. *J Reprod Immunol* 52: 45-59; Welters M J, et al. 2003. Frequent display of human papillomavirus type 16 E6-specific memory t-Helper cells in the healthy population as witness of previous viral encounter. *Cancer Res* 63: 636-41; Nakagawa M, et al. 2000. Persistence of human papillomavirus type 16 infection is associated with lack of cytotoxic T lymphocyte response to the E6 antigens. *J Infect Dis* 182: 595-8; van der Burg S H, et al. 2002. The status of HPV16-specific T-cell reactivity in health and disease as a guide to HPV vaccine development. *Virus Res* 89: 275-84). To date, however, the majority of therapeutic HPV vaccines have been designed to elicit tumor-specific CTL responses (Ressing M E, et al. 2000. Detection of T helper responses, but not of human papillomavirus-specific cytotoxic T lymphocyte responses, after peptide vaccination of patients with cervical carcinoma. *J Immunother* 23: 255-66; Kaufmann A M, et al. 2002. Safety and immunogenicity of TA-HPV, a recombinant vaccinia virus expressing modified human papillomavirus (HPV)-16 and HPV-18 E6 and E7 genes, in women with progressive cervical cancer. *Clin Cancer Res* 8: 3676-85; Garcia F, et al. 2004. ZYC101a for treatment of high-grade cervical intraepithelial neoplasia: a randomized controlled trial. *Obstet Gynecol* 103: 317-26). Unfortunately, only disappointing clinical outcomes have been observed, with the exception of one study with synthetic long peptides in vulvar intraepithelial neoplasia (Kenter G G, et al. 2009. Vaccination against HPV-16 oncoproteins for vulvar intraepithelial neoplasia. *N Engl J Med* 361: 1838-47). Exclusive targeting of HLA (human leukocyte antigen) class I-restricted CTL HPV epitopes, without involving specific T-cell help, can lead to suboptimal and short-lasting CD8+ T cell responses. The lessons learned from these clinical studies lead to a rethinking of therapeutic anti-HPV vaccine design.

Among the eight HPV proteins, E2, E5, E6, and E7 are regarded as being crucial for HPV immune escape and malignant progression. E2 and E5 are expressed soon after infection, prompting HPV immune escape mechanisms and initiating carcinogenic progression (Bellanger S, et al. 2011. Tumor suppressor or oncogene? A critical role of the human papilloma-virus (HPV) E2 protein in cervical cancer progression. *Am J Cancer Res* 1: 373-89; Xue Y, et al. 2012. Loss of HPV16 E2 Protein Expression Without Disruption of the E2 ORF Correlates with Carcinogenic Progression. *Open Virol J* 6: 163-72; Maufort J P, et al. A role for HPV16 E5 in cervical carcinogenesis. *Cancer Res* 70: 2924-31; Ganguly N. 2012. Human papilloma-virus-16 E5 protein: oncogenic role and therapeutic value. *Cell Oncol (Dordr)* 35: 67-76). E6 and E7 as major transforming proteins are constitutively expressed in both premalignant and advanced lesions, making them ideal targets for immunotherapeutic approaches for HPV-induced malignancies (zur Hausen H. 2000. Papillomaviruses causing cancer: evasion from host-cell control in early events in carcinogenesis. *J Natl Cancer Inst* 92: 690-8, Tan S, et al. 2012. Anticancer drugs aimed at E6 and E7 activity in HPV-positive cervical cancer. *Curr Cancer Drug Targets* 12: 170-84).

CD4+ Th cells are known to play critical roles in the generation of CTL immune responses as well as memory T cell responses (Wiesel M, Oxenius A. 2012. From crucial to negligible: functional CD8(+) T-cell responses and their dependence on CD4(+) T-cell help. *Eur J Immunol* 42: 1080-8; Williams M A, et al. 2006. Developing and maintaining protective CD8+ memory T cells. *Immunol Rev* 211: 146-53). CD4+ T cell help prevents peptide-specific tolerance of CD8+ T cells (Shafer-Weaver K A, et al. 2009. Immunity to murine prostatic tumors: continuous provision of T-cell help prevents CD8 T-cell tolerance and activates tumor-infiltrating dendritic cells. *Cancer Res* 69: 6256-64). Further, tumor-specific CD4+ T cells may aid recruitment and cytolytic function of CD8+ T cells in the tumor microenvironment (Bos R, Sherman L A. 2010. CD4+ T-cell help in the tumor milieu is required for recruitment and cytolytic function of CD8+ T lymphocytes. *Cancer Res* 70: 8368-77). Moreover, CD4+ T cells, in absence of CD8+ T cells, may execute direct cytotoxic functions in a peptide-specific and HLA class II-restricted manner (van de Berg P J, et al. Cytotoxic human CD4(+) T cells. *Curr Opin Immunol* 20: 339-43; Brown D M. 2010. Cytolytic CD4 cells: Direct mediators in infectious disease and malignancy. *Cell Immunol* 262: 89-95). This might be relevant to HPV-induced lesions, as HLA class I surface expression can be reduced as a result of HPV immune evasion strategies (Grabowska A K, Riemer A B. 2012. The invisible enemy—how human papillomaviruses avoid recognition and clearance by the host immune system. *Open Virol J* 6: 249-56). In contrast, HLA class II molecules are expressed in high-grade cervical lesions and cervical carcinoma (Coleman N, Stanley M A. 1994. Analysis of HLA-DR expression on keratinocytes in cervical neoplasia. *Int J Cancer* 56: 314-9; Zhou J H, et al. 2006. Altered expression of cellular membrane molecules of HLA-DR, HLA-G and CD99 in cervical intraepithelial neoplasias and invasive squamous cell carcinoma. *Life Sci* 78: 2643-9). It has further been shown that the most effective induction of CTL immune responses requires T helper cells recognizing the same cognate antigen, rather than an unrelated Th stimulus (Bennett S R, et al. 1997. Induction of a CD8+ cytotoxic T lymphocyte response by cross-priming requires cognate CD4+ T cell help. *J Exp Med* 186: 65-70). Therefore, the inventors believe that for rational design of immunotherapeutic approaches against HPV-mediated lesions is beneficial to identify and provide CD4+ T helper cell epitopes derived from HPV target antigens. Most studies on identification of HPV-specific Th epitopes so far have been focusing on E6 and E7 as target antigens and overlapping peptide pools have been used rather than defined peptide epitopes (for review see Wang X, et al. A novel CD4 T-cell epitope described from one of the cervical cancer patients vaccinated with HPV 16 or 18 E7-pulsed dendritic cells. *Cancer Immunol Immunother* 58: 301-8; Welters M J, et al. 2006. Detection of human papillomavirus type 18 E6 and E7-specific CD4+ T-helper 1 immunity in relation to health versus disease. *Int J Cancer* 118: 950-6; Peng S, et al. 2007. HLA-DQB1*02-restricted HPV-16 E7 peptide-specific CD4+ T-cell immune responses correlate with regression of HPV-16-associated high-grade squamous intraepithelial lesions. *Clin Cancer Res* 13: 2479-87; van der Burg S H, et al. 2001. Natural T-helper immunity against human papillomavirus type 16 (HPV16) E7-derived peptide epitopes in patients with HPV16-positive cervical lesions: identification of 3 human leukocyte antigen class II-restricted epitopes. *Int J Cancer* 91: 612-8; Gallagher K M, Man S. 2007. Identification of HLA-DR1- and HLA-DR15-restricted human papillomavirus type 16 (HPV16) and HPV18 E6 epitopes recognized by CD4+ T cells from healthy young women. *J Gen Virol* 88: 1470-8). Although successful, these approaches of systematic T cell epitope mapping are costly and time-consuming, as they require synthesis and several rounds of screening of peptides spanning the full length of the target antigen.

U.S. Pat. No. 8,252,893 B2 describes CD8 T cell epitopes in the E6 and E7 protein of Human Papilloma-virus (HPV). U.S. Pat. No. 7,026,443 B1 discloses human papillomavirus (HPV) epitopes, pharmaceutical compositions and methods of use in the prevention and treatment of HPV infection. EP2167137A1 discloses HPV polyepitope constructs and the use thereof for the prevention and/or treatment of HPV infection.

The identification and characterization of HPV-associated antigens recognized by CD4-positive T cells (ligand: MHC class II molecule+peptide epitope) is important for the further development of HPV vaccines. It is therefore an object of the present invention, to provide novel amino acid sequences for HPV-derived peptides that are able to bind to MHC complexes of class II.

In a first aspect thereof, the invention provides a peptide comprising a sequence selected from the group of SEQ ID Nos. 26, 17, 28, 30, 1 to 16, 18 to 25, 27, 29, and 31 or a variant thereof which is 80% homologous, preferably 90%, and most preferred 95% homologous to any of SEQ ID Nos. 26, 17, 28, 30, 1 to 16, 18 to 25, 27, 29, and 31, wherein said peptide or variant thereof has the ability to bind to a molecule of the human major histocompatibility complex (MHC) class-II. In other variants, one or two amino acids at the N- and/or C-terminal end of a sequence selected from the group of SEQ ID Nos. 26, 17, 28, 30, 1 to 16, 18 to 25, 27, 29, and 31 can be replaced with another amino acid (preferably having the same or similar characteristics), wherein said variant maintains the ability to bind to a molecule of the human major histocompatibility complex (MHC) class-II, preferably the same as the underlying sequence selected from the group of SEQ ID Nos. 26, 17, 28, 30, 1 to 16, 18 to 25, 27, 29, and 31 (see also below).

In the present invention, the term "homologous" refers to the degree of identity between sequences of two amino acid sequences, i.e. peptide or polypeptide sequences. The aforementioned "homology" is determined by comparing two sequences aligned under optimal conditions over the sequences to be compared. The sequences to be compared herein may have an addition or deletion (for example, gap and the like) in the optimum alignment of the two sequences. Such a sequence homology can be calculated by creating an alignment using, for example, the ClustalW algorithm (Nucleic Acid Res., 22(22): 4673 4680 (1994)). Commonly available sequence analysis software, more specifically, Vector NTI, GENETYX or analysis tools provided by public databases, such as e.g. http://dragon.bio.purdue.edu/bioinfolinks/ may also be used.

Table A shows the peptides according to the invention, and their respective SEQ ID NOs.

| SEQ ID NO: | Peptide Sequence |
| --- | --- |
| 1 | PRKLPQLCTELQTTI |
| 2 | QQLLRREVYDFAFRD |
| 3 | FRDLCIVYRDGNPYA |
| 4 | LKFYSKISEYRHYCY |
| 5 | GTTLEQQYNKPLCDL |
| 6 | KQRFHNIRGRWTGRC |
| 7 | MLDLQPETTDLYCYE |
| 8 | STLRLCVQSTHVDIR |
| 9 | TLRLCVQSTHVDIRT |
| 10 | STHVDIRTLEDLLMG |

| SEQ ID NO: | Peptide Sequence |
|---|---|
| 11 | HVDIRTLEDLLMGTL |
| 12 | IRTLEDLLMGTLGIV |
| 13 | RDHIDYWKHMRLECA |
| 14 | FKHINHQVVPTLAVS |
| 15 | VPTLAVSKNKALQAI |
| 16 | QLTLETIYNSQYSNE |
| 17 | LEVYLTAPTGCIKKH |
| 18 | GLYYVHEGIRTYFVQ |
| 19 | PEIIRQHLANHPAAT |
| 20 | ILTAFNSSHKGRINC |
| 21 | IVHLKGDANTLKCLR |
| 22 | CLRYRFKKHCTLYTA |
| 23 | DQFLSQVKIPKTITV |
| 24 | MTNLDTASTTLLACF |
| 25 | RPLLLSVSTYTSLIL |
| 26 | LLSVSTYTSLILLVL |
| 27 | LVLVLWITAASAFRC |
| 28 | ASAFRCFIVYIVFVY |
| 29 | FIVYIVFVYIPLFLI |
| 30 | VYIPLFLIHTHARFL |
| 31 | IPLFLIHTHARFLIT |

Preferred are the following sequences (table A1):

| SEQ ID NO: | Peptide Sequence |
|---|---|
| 3 | FRDLCIVYRDGNPYA |
| 4 | LKFYSKISEYRHYCY |
| 7 | MLDLQPETTDLYCYE |
| 9 | TLRLCVQSTHVDIRT |
| 12 | IRTLEDLLMGTLGIV |
| 17 | LEVYLTAPTGCIKKH |
| 18 | GLYYVHEGIRTYFVQ |
| 26 | LLSVSTYTSLILLVL |
| 28 | ASAFRCFIVYIVFVY |
| 30 | VYIPLFLIHTHARFL |

Most preferred are the following sequences (table A2):

| SEQ ID NO: | Peptide Sequence |
|---|---|
| 4 | LKFYSKISEYRHYCY |
| 7 | MLDLQPETTDLYCYE |
| 9 | TLRLCVQSTHVDIRT |
| 18 | GLYYVHEGIRTYFVQ |
| 26 | LLSVSTYTSLILLVL |

Thus, the invention also relates to a combination of peptides according to the invention, comprising at least two, preferably three, four or five peptides consisting of an amino acid sequence selected from the group of SEQ ID Nos. 26, 9, 7, 4, and 18, in particular in the form of a vaccine such as, for example, a cancer vaccine.

In the present study, with the help of immuno-bioinformatic approaches, the inventors identified several candidate HPV16 E2-, E5-, E6-, and E7-derived CD4+ T cell epitopes promiscuously presented by multiple HLA-DR alleles and evaluated their immunogenicity in healthy individuals. The inventors here present an approach to identify promiscuous HPV16-derived CD4+ T helper epitopes, which are able to induce T cell immunity in a large proportion of the population. To this end, the inventors combined HLA class II epitope prediction servers with ex vivo immunological evaluation to identify HPV16 E2-, E5-, E6-, and E7-derived CD4+ T cell epitopes. Candidate selected HPV16-derived epitopes were found to be restricted by up to nine out of eleven tested HLA-DR molecules. Furthermore, they were found to induce frequent and robust HPV16 peptide-specific T cell responses in the healthy donors, as monitored by IFN-γ ELISPOT and cytokine secretion assays. The observed HPV16 peptide-specific immunity was of the Th1 phenotype, and not associated with CD4+ regulatory T cells. Therefore, the inventors conclude that the identified T helper epitopes are valuable candidates for the development of a comprehensive therapeutic HPV vaccine.

By a "variant" of the given amino acid sequence the inventors mean that the side chains of, for example, one or two of the amino acid residues are altered (for example by replacing them with the side chain of another naturally occurring amino acid residue or some other side chain) so that the peptide is still able to bind to an HLA molecule in substantially the same way as a peptide consisting of the given amino acid sequence. For example, a peptide may be modified so that it at least maintains, if not improves, the ability to interact with and bind a suitable MHC molecule, such as HLA-DR, and so that it at least maintains, if not improves, the ability to generate activated CTL that can recognize and kill cells that express a polypeptide containing an amino acid sequence as defined in the aspects of the invention.

Those amino acid residues that are not essential to interact with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide) which includes the amino acid sequences or a portion or variant thereof as given.

It is furthermore known for MHC-class II presented peptides that these peptides are composed of a "core sequence" having a certain HLA-specific amino acid motif and, optionally, N- and/or C-terminal extensions which do not interfere with the function of the core sequence (i.e. are deemed irrelevant for the interaction of the peptide and all or a subset of T-cell clones recognizing the natural counterpart). The N- and/or C-terminal extensions can, for example, be between 1 to 10 amino acids in length, respectively. These peptides can be used either directly to load MHC class II molecules or the sequence can be cloned into the vectors according to the description herein below. As these peptides constitute the final product of the processing of larger peptides within the cell, longer peptides can be used as well. The peptides of the invention may be of any size, but typically they may be less than 5.000 in molecular weight. In terms of the number of amino acid residues, the peptides of the invention may have fewer than 50 residues. Accordingly the present invention also provides peptides and variants thereof wherein the peptide or variant has an overall length of between 15 and 50, preferably between 15 and 30, and most preferred between 15 and 20 amino acids, namely 15, 16, 17, 18, 19, or 20 amino acids Binding of a peptide or a variant to a MHC complex may be tested by methods known in the art, for example those described in example 4 of the present invention or those described in the literature for different MHC class II alleles (e.g. Vogt A B, et al. Ligand motifs of HLA-DRB5*0101 and DRB1*1501 molecules delineated from self-peptides; J Immunol. 1994; 153(4):1665-1673; Malcherek G, et al. Analysis of allele-specific contact sites of natural HLA-DR17 ligands; J Immunol. 1994; 153(3):1141-1149; Manici S, et al. Melanoma cells present a MAGE-3 epitope to CD4(+) cytotoxic T cells in association with histocompatibility leukocyte antigen DR11; J Exp Med. 1999; 189(5): 871-876; Hammer J, et al. Peptide binding specificity of HLA-DR4 molecules: correlation with rheumatoid arthritis association; J. Exp Med. 1995 181(5):1847-1855; Tompkins S M, Rota P A, Moore J C, Jensen P E; A europium fluoroimmunoassay for measuring binding of antigen to class II MHC glycoproteins; J Immunol Methods. 1993; 163(2): 209-216; Boyton R J, et al. Glutamic acid decarboxylase T lymphocyte responses associated with susceptibility or resistance to type I diabetes: analysis in disease discordant human twins, non-obese diabetic mice and HLA-DQ transgenic mice; Int Immunol. 1998 (12):1765-1776).

The peptides of the present invention or variants thereof are expected to stimulate CD4+ T cells.

In a particularly preferred embodiment of the invention the peptide consists or consists essentially of an amino acid sequence according to SEQ ID Nos. 26, 17, 28, 30, 1 to 16, 18 to 25, 27, 29, and 31. "Consisting essentially of" shall mean that a peptide according to the present invention, in addition to the sequence according to any of SEQ ID Nos. 26, 17, 28, 30, 1 to 16, 18 to 25, 27, 29, and 31 or a variant thereof, contains additional N- and/or C-terminally located stretches of amino acids that are not necessarily forming part of the peptide that functions as an epitope for MHC molecules epitope.

In a particularly preferred embodiment of the invention, the peptide of the invention has an $IC_{50}$: 60≤1000 nM, and preferably an $IC_{50}$≤60 nM for an HLA-DR allele.

In addition the peptide or variant may be modified further to improve stability and/or binding to MHC molecules to elicit a stronger immune response. Methods for such an optimization of a peptide sequence are well known in the art and include, for example, the introduction of reverse peptide bonds or non-peptide bonds.

A non-peptide bond is, for example, —$CH_2$—NH, —$CH_2CH_2$—, —CH=CH—, —$COCH_2$—, —CH(OH)$CH_2$—, and —$CH_2SO$—. U.S. Pat. No. 4,897,445 provides a method for the solid phase synthesis of non-peptide bonds (—$CH_2$—NH) in polypeptide chains that involves polypeptides synthesized by standard procedures and the non-peptide bond synthesized by reacting an amino aldehyde and an amino acid in the presence of $NaCNBH_3$.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley & Sons NY 1995-2000) for more extensive methodology relating to chemical modification of proteins.

Generally, peptides and variants (at least those containing peptide linkages between amino acid residues) may be synthesized by the Fmoc-polyamide mode of solid-phase peptide synthesis as disclosed by Lu et al J. Org. Chem. 1981, 46, 3433, and references therein, as well as through other methods known in the art. Purification may be effected by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

A further aspect of the invention provides a nucleic acid (e.g. polynucleotide) encoding a peptide or variant of the invention. The polynucleotide may be e.g. DNA, cDNA, PNA, CNA, RNA, mRNA, and siRNA or combinations thereof, either single- and/or double-stranded, or native or stabilised forms of polynucleotides, such as e.g. polynucleotides with a phosphorothiate backbone, and it may or may not contain introns so long as it codes for the peptide. Of course, only peptides containing naturally occurring amino acid residues joined by naturally occurring peptide bonds are encodable by a polynucleotide. A still further aspect of the invention provides an expression vector capable of expressing a polypeptide according to the invention. A variety of methods have been developed to operably link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

If viral vectors are used, herpes-, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

In another embodiment the peptide according to the invention, the nucleic acid according to the invention or the expression vector according to the invention are used in medicine. For example, the peptide or its variant may be prepared for intravenous (i.v.) injection, subcutaneous (s.c.) injection, intradermal (i.d.) injection, intraperitoneal (i.p.) injection, intramuscular (i.m.) injection. Preferred routes of peptide injection are s.c., i.d., i.p., i.m., and i.v. Preferred routes of DNA injection are i.d., i.m., s.c., i.p. and i.v. Doses of e.g. between 50 µg and 1.5 mg, preferably 125 µg to 500 µg, of peptide or DNA may be given and will depend from the respective peptide or DNA.

Preferably, the peptides of the invention are produced synthetically, or at least in part synthetically, using well-established peptide synthesis technology.

The present invention also relates to a host cell transformed with a polynucleotide vector construct of the present invention. The host cell thus comprises the nucleic acid according to the invention or the expression vector according to the invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. Transformation of appropriate cell hosts with a DNA construct of the present invention is accomplished by well-known methods that typically depend on the type of vector used.

A further aspect of the invention provides a method of producing a peptide or its variant. The method comprises culturing the host cell of the invention, and isolating the peptide from the host cell or the culture medium.

Another aspect of the present invention relates to a vaccine comprising the host cells as described herein, which in a preferred embodiment is a life vaccine. In such an embodiment, the host cell can be an antigen presenting cell, in particular a dendritic cell. APCs loaded with a recombinant fusion protein containing prostatic acid phosphatase (PAP) are approved for the treatment of prostate cancer (Sipuleucel-T) (see, e.g., Cheever M A, Higano C S. PROVENGE (Sipuleucel-T) in prostate cancer: the first FDA-approved therapeutic cancer vaccine. Clin Cancer Res. 2011 Jun. 1; 17(11):3520-6; Epub 2011 Apr. 6).

Another aspect of the present invention is an in vitro method for inducing activated T helper ($T_H$) cells, comprising contacting in vitro $T_H$ cells with antigen loaded human class II MHC molecules expressed on the surface of a suitable antigen-presenting cell for a period of time sufficient to activate said $T_H$ cells in an antigen specific manner, wherein said antigen is a peptide according to the invention. Preferably, a sufficient amount of the antigen is used with an antigen-presenting cell.

The MHC class II molecules may be expressed on the surface of any suitable cell. Thus, the antigen-presenting cell (or stimulator cell) typically has MHC class II molecules on its surface. The MHC class II molecule may readily be loaded with the selected antigen in vitro. In case of MHC II epitopes as antigens, the T cells are CD4-positive T-helper cells.

A number of methods for generating activated T cells in vitro are described in the respective literature.

The activated $T_H$ cells that are directed against the peptides of the invention are useful in therapy. Thus, a further aspect of the invention provides activated $T_H$ cells, produced and obtainable by the method according to the invention, which selectively recognizes a cell which expresses an HPV polypeptide comprising an amino acid sequence according to SEQ ID Nos. 26, 17, 28, 30, 1 to 16, 18 to 25, 27, 29, or 31.

The $T_H$ cells of the invention may be used as active ingredients in a therapeutic composition. Thus the invention also provides a method of killing target cells in a patient where the target cells express a polypeptide comprising an amino acid sequence of the invention. The method comprises administering to the patient an effective number of $T_H$ cells as defined above.

$T_H$ cells may be obtained by methods known in the art, e.g. those described above.

Any molecule of the invention, i.e. the peptide, nucleic acid, expression vector, cell, activated $T_H$ cells, T-cell receptor or the nucleic acid encoding it is useful for the treatment of HPV-related disorders, characterized by cells escaping an immune response. Therefore any molecule of the present invention may be used as medicament or in the manufacture of a medicament. The molecule may be used by itself or combined with other molecule(s) of the invention or (a) known molecule(s).

An important aspect of the present invention is therefore a pharmaceutical preparation, comprising at least one of the peptide according to the invention, the nucleic acid according to the invention, the expression vector according to the invention, the host cell according to the invention, the activated $T_H$ lymphocyte according to the invention, and a pharmaceutically acceptable excipient, wherein preferably said pharmaceutical preparation is a vaccine.

Preferably the medicament is a vaccine. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient. If the nucleic acid is administered to cells in vitro, it may be useful for the cells to be transfected so as to co-express immune-stimulating cytokines, such as interleukin-2 The peptide may be substantially pure, or combined with an immune-stimulating adjuvant (see below) or used in combination with immune-stimulatory cytokines, or be administered with a suitable delivery system, for example nanoparticles or liposomes. The peptide may also be conjugated to a suitable carrier such as keyhole limpet haemocyanin (KLH) or mannan (see WO 95/18145 and Longenecker et al. (1993) Ann. NY Acad. Sci. 690, 276-291).

Thus, in another aspect of the invention, the peptide according to the invention is part of a fusion protein or fusion molecule, e.g. with a TLR ligand.

In one aspect of the invention, the vaccine comprises at least one peptide, preferably two to 31, more preferably two to 25, even more preferably two to 15 and most preferably two, three, four, five, six, seven, eight, nine, ten, eleven, twelve or thirteen peptides of the invention or additional peptides. The peptide(s) may be derived from one or more specific HPV antigen, and may bind to MHC class I and/or class II molecules.

Particularly preferred vaccines include peptides according to the present invention that show an $IC_{50} \leq 60$ nM for an HLA-DR allele.

More preferred is an HPV vaccine comprising at least one, preferably all, of the following peptides (table A3):

| SEQ ID NO: | Peptide Sequence |
| --- | --- |
| 3 | FRDLCIVYRDGNPYA |
| 4 | LKFYSKISEYRHYCY |
| 7 | MLDLQPETTDLYCYE |
| 9 | TLRLCVQSTHVDIRT |
| 12 | IRTLEDLLMGTLGIV |
| 17 | LEVYLTAPTGCIKKH |
| 18 | GLYYVHEGIRTYFVQ |
| 26 | LLSVSTYTSLILLVL |
| 28 | ASAFRCFIVYIVFVY |
| 30 | VYIPLFLIHTHARFL |

Most preferred is an HPV vaccine comprising at least one, preferably all, of the following peptides (table A4):

| SEQ ID NO: | Peptide Sequence |
| --- | --- |
| 4 | LKFYSKISEYRHYCY |
| 7 | MLDLQPETTDLYCYE |
| 9 | TLRLCVQSTHVDIRT |
| 18 | GLYYVHEGIRTYFVQ |
| 26 | LLSVSTYTSLILLVL |

The medicament of the invention may also include one or more adjuvants. Adjuvants are substances that non-specifically enhance or potentiate the immune response (e.g. immune responses mediated by CTLs and helper-T ($T_H$) cells to an antigen, and would thus be considered useful in the medicament of the present invention.

Suitable adjuvants include, but are not limited to aluminum salts, TLR agonists, or GM-CSF or other commercial adjuvants.

When the peptides of the invention are used in a vaccine or medicament of the invention, they are present as a salt, such as for example, but not limited to an acetate salt or a chloride salt.

Another aspect of the invention then relates to the peptide according to the invention, the nucleic acid according to the invention, the expression vector according to the invention, the host cell according to the invention, the activated $T_H$ cell according to the invention, or the pharmaceutical preparation according to the invention for use in the treatment of HPV infection, and HPV-related pre-malignancies and/or malignancies.

Yet another aspect of the invention relates to a method of killing target cells in a patient which target cells express an HPV polypeptide comprising an amino acid sequence as given for the peptides herein, the method comprising administering to the patient an effective number of $T_H$ cell according to the invention.

In yet another aspect thereof, the present invention relates to a kit comprising (a) a container that contains a pharmaceutical composition as described above, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. Said kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contains instructions on or associated with the container that indicates directions for reconstitution and/or use. For example, the label may indicate that the lyophilized formulation is to reconstituted to peptide concentrations as described above.

Numerous reports demonstrate the importance of both CD8+ and CD4+ T cells in the clearance of HPV infection as well as in the protection against developing HPV-associated malignancies (10-13). However, the development of successful anti-HPV immunotherapy has proved to be a challenging task. Recently, there has been considerable interest to identify HPV E6 and E7-derived CD4+ T helper cell epitopes using overlapping peptide pools and to include them in therapeutic peptide-based therapeutic vaccine design (34-38). The inventors' approach in the current work was to use computational HLA class II prediction algorithms to define a 15-mer HPV16-derived CD4+ T cell epitopes that bind promiscuously to the binding groove of multiple HLA-DR molecules. The inventors performed predictions for eleven alleles, namely DRB1*0101, DRB1*0301, DRB1*0401, DRB1*0701, DRB1*0901, DRB1*1101, DRB1*1302, DRB1*1501, DRB3*0101, DRB4*0101 and DRB5*0101. Candidate promiscuous epitopes were evaluated in vitro for their potential to elicit immune responses in healthy subjects. As most sexually active individuals are infected transiently with at least one high-risk HPV type during their life (Woodman C B, Collins S I, Young L S. 2007. The natural history of cervical HPV infection: unresolved issues. *Nat Rev Cancer* 7: 11-22, Evander M, et al. 1995. Human papillomavirus infection is transient in young women: a population-based cohort study. *J Infect Dis* 171: 1026-30), previous HPV exposure of the donors is likely.

The use of prediction servers has several advantages over using overlapping peptide pools. Testing overlapping epitopes spanning the full length of a protein is a time-consuming approach even when testing only one HLA type, but even more so when several HLA molecules have to be interrogated for the identification of promiscuously binding epitopes. Thus, in the present study, the inventors took advantage of two HLA class II epitope prediction servers, SYFPEITHI and NetMHCII. This allowed them to screen in silico for candidate peptides binding to several HLA class II molecules. Only peptides predicted to bind to five or more HLA-DR molecules were further analyzed, thus focusing immune assays to the most promising candidates. As the accuracy of prediction servers is not absolute, it is recommendable to use more than one, to ensure that no potential binder is missed. Also in this study, it can be seen that the results from the two prediction servers were not completely consistent. The combined use of both let to the inclusion of peptides that would not have been found by applying only one prediction algorithm.

Up to now, most studies focused on the identification of epitopes derived from the HPV oncoproteins E6 and E7, in the context of peptide-based immunotherapy against advanced lesions in the patients (Wang X, et al. 2009. A novel CD4 T-cell epitope described from one of the cervical cancer patients vaccinated with HPV 16 or 18 E7-pulsed dendritic cells. *Cancer Immunol Immunother* 58: 301-8; Welters M J, et al. 2006. Detection of human papillomavirus type 18 E6 and E7-specific CD4+ T-helper 1 immunity in relation to health versus disease. *Int J Cancer* 118: 950-6; Peng S, et al. 2007. HLA-DQB1*02-restricted HPV-16 E7 peptide-specific CD4+ T-cell immune responses correlate with regression of HPV-16-associated high-grade squamous intraepithelial lesions. *Clin Cancer Res* 13: 2479-87; van der Burg S H, et al. 2001. Natural T-helper immunity against human papillomavirus type 16 (HPV16) E7-derived peptide epitopes in patients with HPV16-positive cervical lesions: identification of 3 human leukocyte antigen class II-restricted epitopes. *Int J Cancer* 91: 612-8; Gallagher K M, Man S. 2007. Identification of HLA-DR1- and HLA-DR15-restricted human papillomavirus type 16 (HPV16) and HPV18 E6 epitopes recognized by CD4+ T cells from healthy young women. *J Gen Virol* 88: 1470-8). To the best of the inventors' knowledge, there is only one study reporting CD4+ T cell epitopes for HPV16 E2 (de Jong A, et al. 2002. Frequent detection of human papillomavirus 16 E2-specific T-helper immunity in healthy subjects. *Cancer Res* 62: 472-9), and no studies on E5-derived T helper epitopes. None of these studies deal with the identification of promiscuous CD4+ T cell epitopes. As the inclusion of such epitopes in any peptide-based therapeutic HPV vaccine is expected to increase immunogenicity and efficacy, the inventors here aimed to identify promiscuous T helper epitopes derived from HPV16 E2, E5, E6 and E7.

Overall, the inventors found that 13 out of the 31 predicted promiscuously binding HPV16-derived HLA class II peptides (Table 1) were recognized by at least 30% of healthy donors in short-term ex vivo ELISPOT assays (Tables 2 and 3). The inventors identified seven novel HPV16 15-mer CD4+ T cell epitopes, namely E2/76-90, E5/33-48, E5/45-60, E5/54-69, E5/60-74, E5/67-81 and E7/12-26. The epitopes E6/54-68, E6/74-88, E7/64-78, E7/71-85, E2/99-113 and E2/156-170 are part of previously reported long peptides (Welters M J, et al. 2003. Frequent display of human papillomavirus type 16 E6-specific memory t-Helper cells in the healthy population as witness of previous viral encounter. *Cancer Res* 63: 636-41, Wang X, et al. A novel CD4 T-cell epitope described from one of the cervical cancer patients vaccinated with HPV 16 or 18 E7-pulsed dendritic cells. *Cancer Immunol Immunother* 58: 301-8, Peng S, et al. 2007. HLA-DQB1*02-restricted HPV-16 E7 peptide-specific CD4+ T-cell immune responses correlate with regression of HPV-16-associated high-grade squamous intraepithelial lesions. *Clin Cancer Res* 13: 2479-87, de Jong A, et al. 2002. Frequent detection of human papillomavirus 16 E2-specific T-helper immunity in healthy subjects. *Cancer Res* 62: 472-9), supporting the inventors' approach of epitope detection. Each peptide was predicted to bind to five to nine different HLA class II molecules out of the eleven tested in this study, and found to elicit immune responses in individuals carrying the respective HLA class II alleles (Table 4). Only three subjects showed reactivity towards a peptide that was not predicted to bind to any of his/her HLA-DR molecules. This reactivity could be due to HLA-DP or -DQ peptide presentation, or HLA class I restricted epitopes contained in the respective 15-mers (see below). Another interesting finding was the high proportion of HPV16 E7-specific CD4+ T cell responses in the cohort, although it has been reported that E7-reactivity is rarely observed in healthy individuals (Welters M J, et al. 2003. Frequent display of human papillomavirus type 16 E6-specific memory t-Helper cells in the healthy population as witness of previous viral encounter. *Cancer Res* 63: 636-41 van der Burg S H, et al. 2001. Natural T-helper immunity against human papillomavirus type 16 (HPV16) E7-derived peptide epitopes in patients with HPV16-positive cervical lesions: identification of 3 human leukocyte antigen class II-restricted epitopes. *Int J Cancer* 91: 612-8; Gallagher K M, Man S. 2007. Identification of HLA-DR1- and HLA-DR15-restricted human papillomavirus type 16 (HPV16) and HPV18 E6 epitopes recognized by CD4+ T cells from healthy young women. *J Gen Virol* 88: 1470-8).

Figure 2:
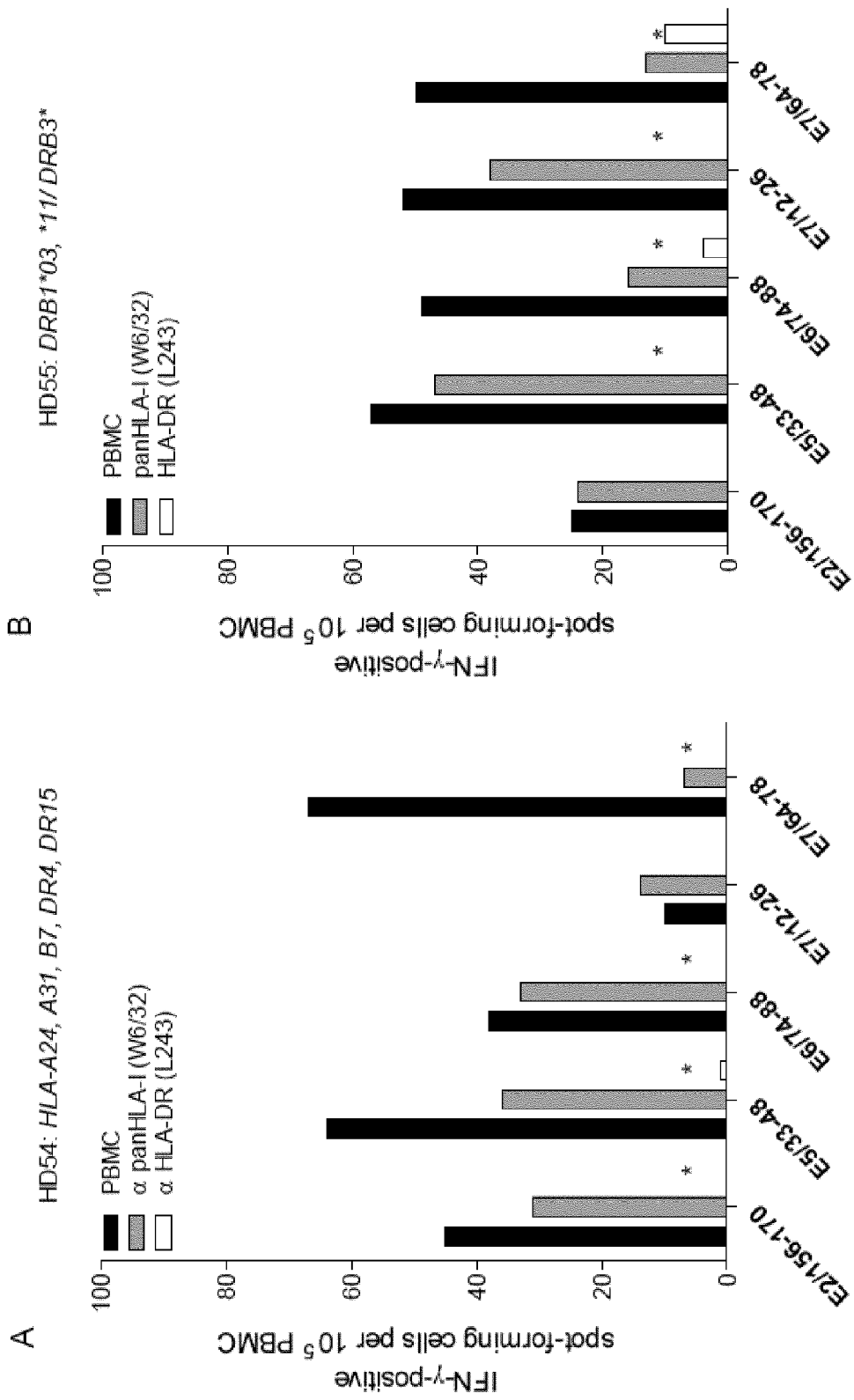

Based on ELISPOT reactivities (FIG. 1), five epitopes were selected for detailed analysis. HLA class II restriction of the HPV16 peptide-specific T cell responses was confirmed by abrogation of IFN-γ production in the presence of an HLA-DR blocking antibody (FIG. 2). Possible HLA-DQ and HLA-DP restriction of the selected peptides was not assessed in the inventors' study. Regarding the phenotype of HPV16 peptide-specific T cell immunity, the inventors' results from CD4+ and CD8+ T cell depletion (FIG. 3) and intracellular cytokine staining experiments provide strong evidence that the responding T cells are indeed CD4+ T cells. The profile of cytokine secretion of HPV16 peptide-specific CD4+ T cells was found to be of the Th1 type (IFN-γ, TNF-α, GM-CSF) (FIG. 4A), which is associated with control and clearance of HPV infections (Scott M, Stites D P, Moscicki A B. 1999. Th1 cytokine patterns in cervical human papillomavirus infection. *Clin Diagn Lab Immunol* 6: 751-5; Bais A G, et al. 2007. Cytokine release in HR-HPV(+) women without and with cervical dysplasia (CIN II and III) or carcinoma, compared with HR-HPV(−) controls. *Mediators Inflamm* 2007: 24147). Moreover, the inventors observed only low percentages of HPV16 peptide-specific CD4+ regulatory T cells (FIG. 4B and FIG. 5), which is also associated with a favorable disease outcome (van der Burg S H, et al. 2007. Association of cervical cancer with the presence of CD4+ regulatory T cells specific for human papillomavirus antigens. *Proc Natl Acad Sci USA* 104: 12087-92; Kim K H, et al. 2012. CD4+ T-cell response against human papillomavirus type 16 E6 protein is associated with a favorable clinical trend. *Cancer Immunol Immunother* 61: 63-70; Visser J, et al. 2007. Frequencies and role of regulatory T cells in patients with (pre)malignant cervical neoplasia. *Clin Exp Immunol* 150: 199-209). As the inventors tested healthy donors who are likely to have cleared HPV infection in their past, these results are promising that the inventors' strategy indeed identifies peptides involved in viral clearance.

CD4+ T cells have recently been reported to be capable of direct cytotoxic functions (van de Berg P J, et al. 2008. Cytotoxic human CD4(+) T cells. *Curr Opin Immunol* 20: 339-43; Brown D M. 2010. Cytolytic CD4 cells: Direct mediators in infectious disease and malignancy. *Cell Immunol* 262: 89-95), therefore perforin/granzyme B release as well as CD107a expression analyses were performed. However, no HPV16-derived peptide-specific CD4+ T cell-mediated cytotoxic activity was observed in this cohort of healthy individuals (data not shown). This observation might reflect the fact that cytotoxic activity of T helper cells arises only during acute or persistent infections or in the presence of malignancies (Brown D M. 2010. Cytolytic CD4 cells: Direct mediators in infectious disease and malignancy. *Cell Immunol* 262: 89-95).

Importantly, it is possible that defined CD4+ T cell epitopes harbor HLA class I-restricted immunogenic regions. HLA class II-restricted epitopes that contain HLA class I epitopes in their sequence could be highly useful for effective peptide-based immunotherapies, as both CD4+ and CD8+ T cell responses may be simultaneously induced.

In summary, the inventors have defined 13 promiscuous 15-mer HPV16-derived CD4+ T cell epitopes, seven of which have not been described before. The inventors show that selected epitopes indeed are promiscuous and immunogenic, inducing Th1 cells in healthy individuals with a diverse genetic background. The inventors conclude that the identified T helper epitopes are candidates for the development of a comprehensive epitope-specific therapeutic HPV vaccine against established premalignant as well as advanced lesions.

The invention will now be described in more detail in the following examples with reference to the accompanying Figures and the sequence listing, nevertheless, without being limited thereto. For the purposes of the present invention, all references as cited herein are incorporated by reference in their entireties. In the Figures, FIG. 1 shows the detection of HPV16 peptide-specific T cell immunity in healthy subjects. The PBMC reactivity of 13 healthy donors was evaluated by stimulating with selected HPV16-derived peptides for 12 days. IFN-γ peptide-specific T cells were analyzed by ELISPOT. Each dot represents the number of positive cells in one individual. Data represent the mean from triplicate wells after background subtraction. Mean responses (±SE) across donors are shown for each peptide. Responses are considered positive (●) if they were at least twofold higher than the background. An open circle (○) represents a non-responder. Percentages represent response rate of tested healthy subjects to the indicated HPV16-derived peptide.

FIG. 2 shows that T cell immunity induced by the selected HPV16-derived peptides is dependent on HLA class II peptide presentation. PBMC obtained from subject HD54 (A) and HD55 (B) were incubated in the presence or absence of anti-HLA-DR or panHLA-I W6/32 antibodies prior the indicated peptide exposure, and responses analyzed by IFN-γ ELISPOT. Data represent the mean result from triplicate wells after background subtraction. Significant inhibition in presence of HLA-DR antibodies compared to non-treated PBMC is indicated by * ($P \leq 0.05$, two-tailed Student's t-test). The HLA genotypes of tested subjects are indicated above the panels.

Figure 3:
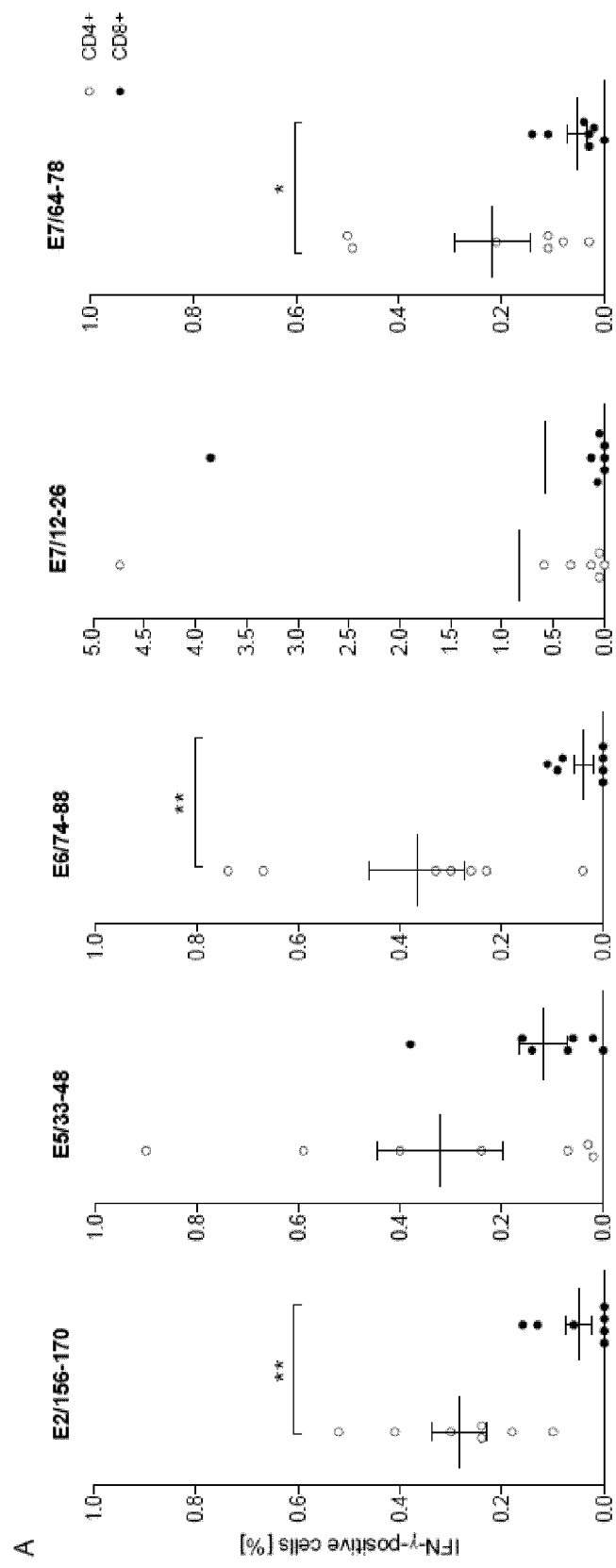
Figure 3:
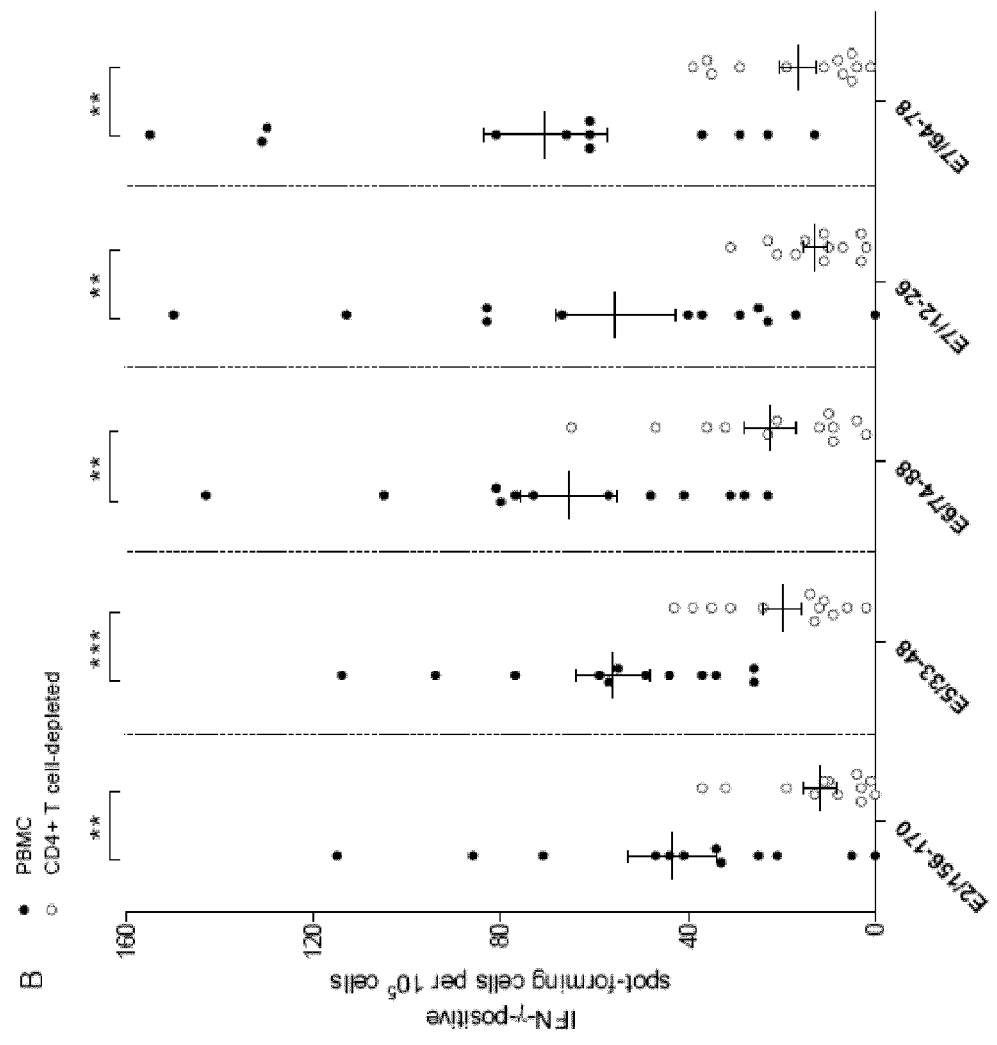
Figure 3:
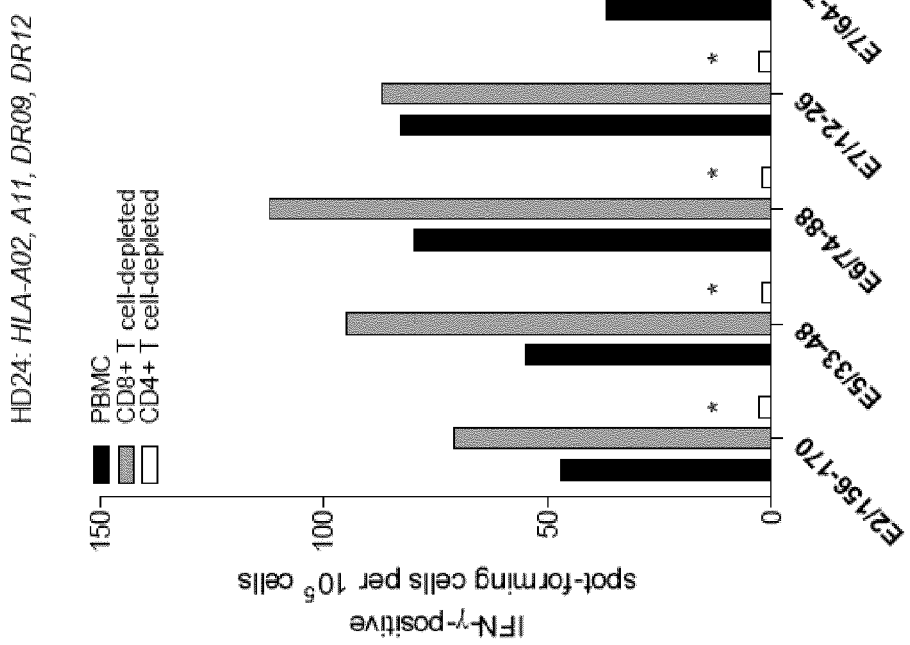
Figure 3:
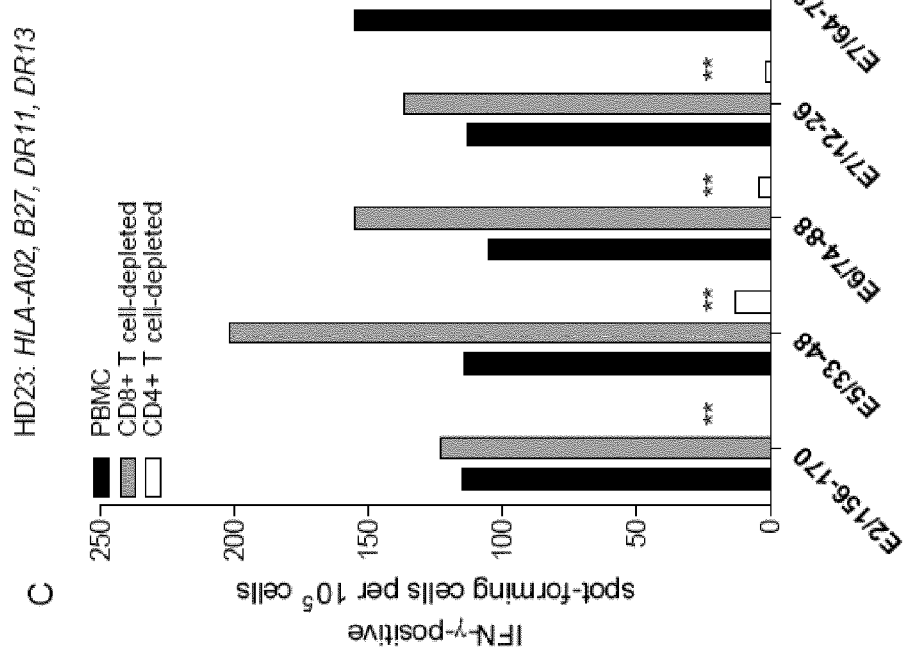

FIG. 3 shows that the induced HPV16 peptide-specific T cell immunity is mediated by CD4+ T cells. PBMC of 7 healthy donors after stimulation with the indicated HPV16-derived peptides were tested by flow cytometry-based IFN-γ intracellular staining (ICS) (A). Each dot represents an individual. Results are presented as percentage of IFN-γ-positive CD4+ (●) or CD8+ (○) cells after background subtraction. (B) PBMC (●) obtained from 12 healthy individuals were depleted of CD4+ T cells (○), stimulated with selected peptides, and analyzed by IFN-γ ELISPOT. Each dot represents an individual. Data represent the mean result from triplicate wells after background subtraction. (C) PBMCs of two subjects (HD23 and HD24) were depleted of either CD4+ or CD8+ T cells prior to peptide exposure as indicated and analyzed by IFN-γ ELISPOT. Data represent the mean result from triplicate wells after background subtraction. The HLA genotypes of tested subjects are indicated above the panels. Mean responses (±SE) are indicated for each peptide. Significant differences are indicated by * ($P \leq 0.05$),  ($P \leq 0.01$) or * ($P \leq 0.001$, two-tailed Student's t-test).

Figure 4:
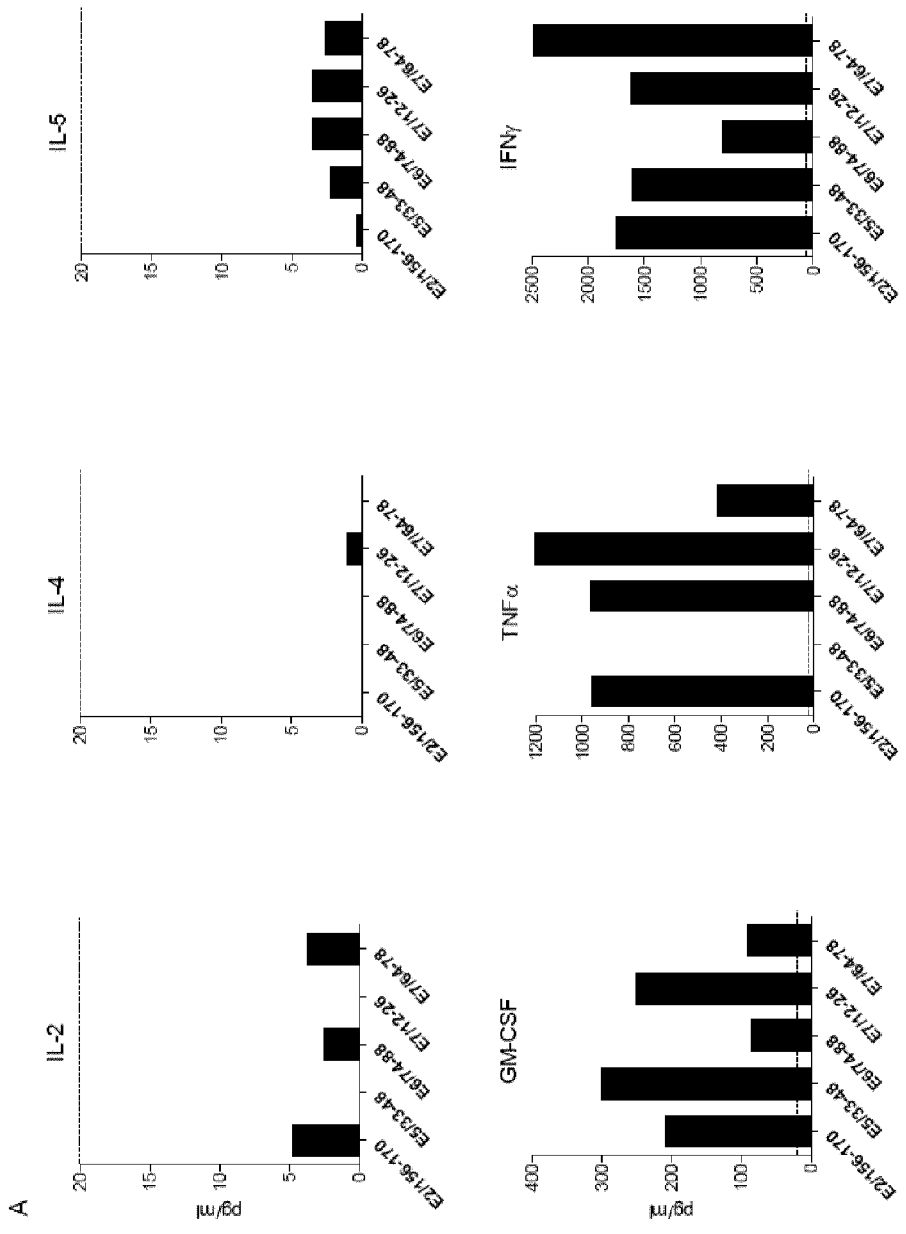
Figure 4:
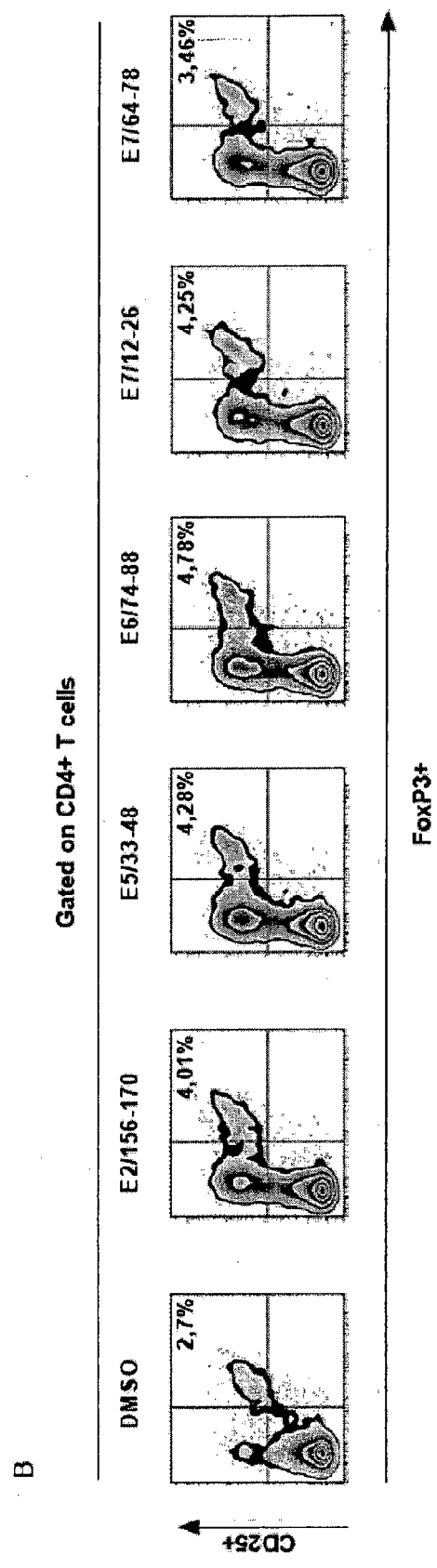

FIG. 4 shows that the induced HPV16 peptide-specific immunity is associated with Th1-type cells but not with CD4+ regulatory T cells. (A) The supernatants of T cell cultures from HD23 were tested 3 days after in vitro stimulation with indicated peptides for the indicated cytokines Data represent the mean result from duplicate wells after background subtraction. The cut-off for positivity is indicated by a dashed line. (B) PBMC were also investigated for presence of CD4+/CD25+/FoxP3+ regulatory T cells after 8 day in vitro stimulation with indicated peptides or without stimulation (DMSO) in a flow cytometry-based assay. Results are presented as percentage of CD25+/FoxP3+ T cells on the counter plot gated on CD4+ T cells. Representative results of one donor (HD 23) are shown. The HLA genotype of the tested subject is indicated above the panel.

Figure 5:
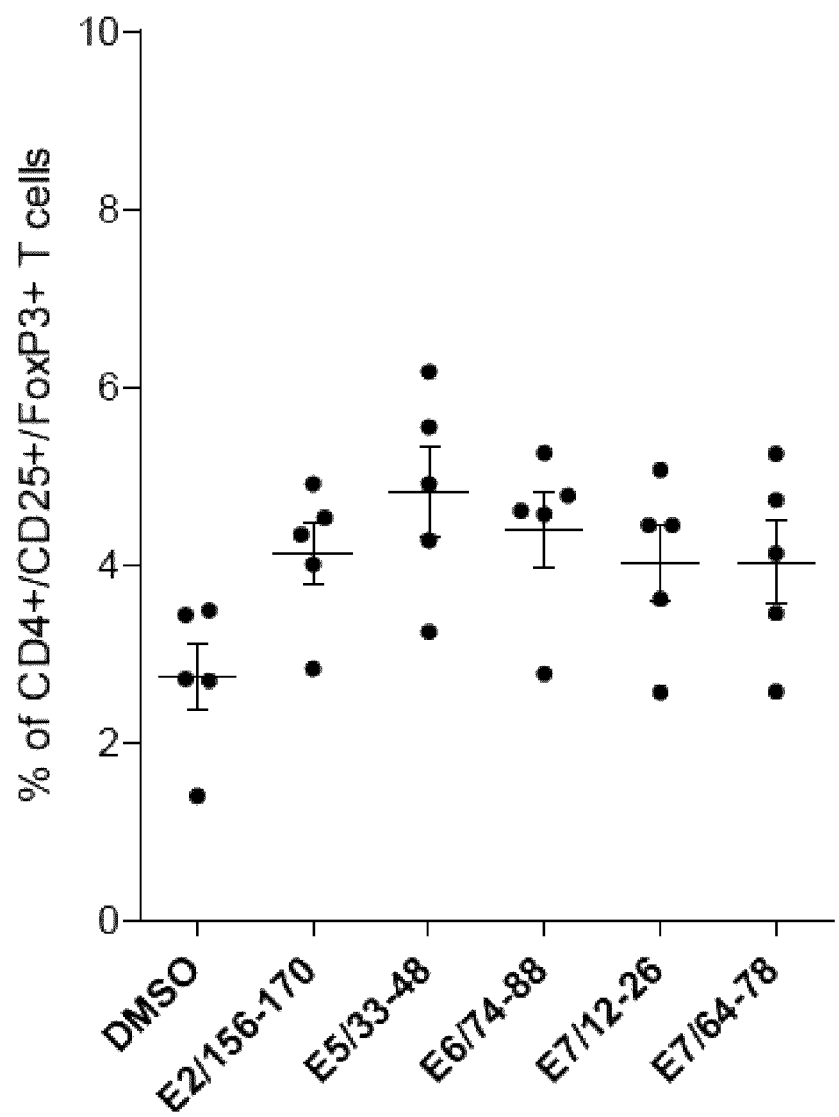

FIG. 5 shows that PBMC of five healthy donors were investigated for presence of CD4+/CD25+/FoxP3+ regulatory T cells after 12 days in vitro stimulation with indicated peptides or without stimulation (DMSO) in a flow cytometry-based assay. Results are presented as percentage of CD25+/FoxP3+ T cells. Each dot represents an individual. Mean responses (±SE) across donors are shown for each peptide.

SEQ ID NO: 1 to 31 show peptide sequences of HPV-related antigens and epitopes according to the invention.

EXAMPLES

Materials and Methods

Prediction of Promiscuous HLA Class II-Binding HPV-Derived Epitopes

An epitope prediction server, SYFPEITHI (http://www.syfpeithi.com) (39) was used for predicting 15-mer Th epitopes in E7 (GenBank: AAD33253.1), E6 (GenBank: AAD33252.1), E5 (GenBank: AA085413.1), and E2 (GenBank: AAD33255.1) proteins of HPV16. The in silico predictions were performed for multiple HLA-DR molecules encoded by DRB1*0101, DRB1*0301, DRB1*0401, DRB1*0701, DRB1*1101 and DRB1*1501 alleles. Higher binding score values indicate higher predicted binding affinity of candidate peptides to the selected HLA-DR allele. To identify promiscuous CD4+ T cell epitopes, for each protein, candidate peptides were ranked according to their predicted binding affinity among the indicated HLA-DR alleles, excluding epitopes harboring more than two cysteine residues. Peptides predicted to bind at least five HLA-DR molecules were selected. In addition, HLA-DR binding epitopes were analyzed for dataset cross-comparison by the recently developed NetMHCII (NN-align) prediction method (Nielsen M, et al. 2010. NetMHCIIpan-2.0—Improved pan-specific HLA-DR predictions using a novel concurrent alignment and weight optimization training procedure. *Immunome Res* 6: 9, Nielsen M, Lund O. 2009. NN-align. An artificial neural network-based alignment algorithm for MHC class II peptide binding prediction. *BMC Bioinformatics* 10: 296) (http://www.cbs.dtu.dk/services/NetMHCII/), which also allows to perform predictions for molecules encoded by DRB1*0901, DRB1*1302, DRB3*0101, DRB4*0101 and DRB5*0101 alleles. In this case, lower $IC_{50}$ nM values indicate higher binding affinity of peptides to a HLA-DR molecule.

Peptides

The 15-mer peptides were synthesized using 9-fluorenylmethoxycarbonyl chemistry, and purified by high-performance liquid chromatography (>95% purity) and validated by mass spectrometry (Genomics and Proteomics Core Facility, German Cancer Research Center (DKFZ), Heidelberg, Germany). Synthetic peptides were reconstituted in DMSO (Sigma, Taufkirchen, Germany) at a concentration of 10 mg/ml, and stored at −80° C. A MHC class II peptide pool (PANATecs, Tubingen, Germany) was included in experiments as a positive control.

Healthy Volunteers and Peripheral Blood T Cell Sample Acquisition

Peripheral blood samples or buffy coats of whole blood from anonymous healthy individuals were obtained from the IKTZ Heidelberg Blood Bank. As these donors are anonymous, no data are available to determine HPV infection status. Peripheral blood mononuclear cells (PBMC) were isolated within 12 h using a standard Ficoll-Hypaque density gradient procedure. PBMC were cultured directly or cryopreserved in RPMI-1640 medium (PAA, Coelbe, Germany) containing 20% fetal bovine serum (FBS) (Bio West, Nuaille, France) and 10% DMSO and stored in the gas phase of liquid nitrogen for later use. The HLA class I and class II haplotypes of the blood donors were typed by the Transplantation and Immunology Laboratory at the Institute of Immunology and Serology, Heidelberg, Germany. Sampling and use of PBMC were in accordance with the Institutional Review Board at DKFZ and the University of Heidelberg, Heidelberg, Germany.

Depletion of CD4+ T Cells from PBMC

PBMC were depleted of CD4+ T cells according to the manufacturer's instruction using anti-CD4 MicroBeads (Miltenyi Biotec, Bergisch Gladbach, Germany). Purity was assessed by flow cytometry. PBMC were effectively (>98%) depleted of CD4+ cells.

T-Cell Culture and IFN-γ ELISPOT Assay

PBMC were used for CD4+ T cell depletion or cultured directly in RPMI-1640 supplemented with 10% FBS, 2 mM L-glutamine, 10 mM HEPES, 100 U/ml penicillin and 100 μg/ml streptomycin (R10 medium). The immunogenicity of candidate HPV16-derived peptides was evaluated by ELISPOT analysis of short-term PBMC cultures. Briefly, PBMC were seeded at a density of $10^6$ cells/well in 24-well plates (Becton Dickinson (BD), Heidelberg, Germany) in 1 ml of R10 medium, in the presence or absence of individual HPV16-derived peptides with a final concentration of 20 μg/ml. As a positive control, PBMC were cultured in the presence of the positive peptide pool (4 μg/ml) or 5 μg/ml of phytohaemagglutinin (PHA; Sigma). On day 5, PBMC were harvested, and seeded in triplicate wells at a density of $10^5$ cells/well on Multiscreen-HA ELISPOT plates (Millipore, Darmstadt, Germany) coated with 2 μg/ml of anti-human IFN-γ antibody 1-D1K (Mabtech AB, Nacka Strand, Sweden). Cells were incubated for another 20 h at 37° C. The ELISPOT assay was developed according to the manufacturer's instructions (Mabtech AB). The number of spots was analyzed with an AID ELISPOT reader (AID Diagnostika, Strassberg, Germany). Specific spots were calculated by subtracting the mean number of spots of the DMSO background control from the mean number of spots of test wells. A peptide-specific T cell response was considered positive when the mean spot number for a given peptide was at least twofold higher than mean background spot number.

In experiments in which selected HPV-derived peptides were further analyzed, the PBMC or depleted PBMC were cultured for 12 days. Briefly, PBMC or depleted PBMC were seeded at a density of $5\times10^5$ to $1\times10^6$ cells/well in 24-well plates in 1 ml of R10 medium supplemented with recombinant human interleukin-7 (rhIL-7, R&D Systems, Wiesbaden, Germany) at a final concentration of 330 U/ml per well. Cells were incubated in the presence of either DMSO (background control), selected HPV16-derived peptides (20 μg/ml) or the positive peptide pool (4 μg/ml). On days 3 and 7, cell culture was supplemented with rhIL-2 (Pepro-Tech, Hamburg, Germany) at a final concentration 20 U/ml per well and the medium was replaced (no rhIL-2) on day 10. Cells were restimulated on day 11 with the indicated peptides (20 μg/ml). On day 12, cultures were analyzed for the presence of peptide-specific T cells by IFN-γ ELISPOT assay as described above.

To block peptide-specific IFN-γ production, anti-HLA-DR antibody L243 (BioLegend, Fell, Germany) or anti-HLA class I antibody W6/32 were added to the cell cultures at a final concentration of 10 μg/ml for 30 min before peptide exposure.

IFN-γ Intracellular Cytokine Staining

PBMC stimulated for 11 days with peptide as described above, were harvested, washed and incubated in the presence of either DMSO or selected HPV16-derived peptide (20 μl/ml). GolgiPlug (1/1000; BD) was added after 1 h for a further 12 h incubation period. The cells were washed and blocked with PBS/10% FBS and next stained for the surface markers CD3-APC, CD4-PE, CD8-FITC (BD). For intracellular staining, cells were fixed and permeabilized using Cytofix/Cytoperm solution according to the manufacturer's instructions (BD). The cells were washed with Perm/Wash buffer (BD) before staining with anti-human IFN-γ eFluor450-conjugated antibody (eBioscience, Frankfurt, Germany). After fixation with 1% formaldehyde, stained cells were analyzed on a FACS Canto II cytometer (BD). Respective isotype controls were used in all experiments. Data analysis was performed with FlowJo (TreeStar, Ashland, Oreg., USA). Identical gates were used for all samples. A response was considered positive for peptide-specific T cells if the response was greater than 0.04% after subtraction of the mean DMSO background.

Cytokine Assays

The supernatants collected on day 3 of the PBMC cultured with or without selected HPV-derived peptides were subjected to cytokine magnetic bead assay Milliplex MAP (Millipore) according to the manufacturer's instructions. The read-out of the assay was performed on a Luminex MAGPIX instrument with xPONENT software (Luminex, Austin, Tex., USA). In this assay, the levels of IFN-γ, TNF-α, GM-CSF, IL-4, IL-5 and IL-2 were determined. A peptide-specific cytokine production was considered positive if (after subtraction of the mean DMSO control) the cytokine concentration was over the cutoff value of 20 pg/ml (50 pg/ml for IFN-γ).

Phenotypic CD4+ T Cell Analysis by Flow Cytometry

PBMC stimulated for 11 days with peptide as described above, were harvested, washed and incubated in the presence of either DMSO or relevant HPV-derived peptide (20 µl/ml). GolgiPlug (1/1000; BD) was added after 1 h for a further 12 h incubation period. The cells were washed and blocked with PBS/10% FBS and next stained for the surface markers CD4-FITC, CD25-APC (BD). For intracellular staining, cells were fixed and permeabilized using Transcription Factor FIX/Perm Buffer according to the manufacturer's instructions (BD). The cells were washed with Perm/Wash buffer (BD) before staining with anti-human FoxP3 PE-conjugated antibody (BD). After fixation with 1% formaldehyde, stained cells were analyzed on a FACS Canto II cytometer (BD).

Statistical Analysis

Statistical analysis was performed using GraphPad Prism 5 Software Inc. Two-tailed Student's t-test with Welch's correction was used to analyze the data. P values≤0.05 were considered significant.

Results

Prediction and Selection of Candidate Peptides Derived from the HPV16 E2, E5, E6 and E7 Proteins with High Binding Potency for Multiple HLA-DR Molecules The inventors' study was designed to identify epitopes binding to multiple HLA-DR alleles, derived from HPV16 early proteins E2, E5, E6 and E7. Therefore the inventors first analyzed the amino acid sequence of the indicated HPV16 proteins using two epitope prediction algorithms (Rammensee H, et al. 1999. SYFPEITHI: database for MHC ligands and peptide motifs. *Immunogenetics* 50: 213-9; Nielsen M, et al. 2010. NetMHCIIpan-2.0—Improved panspecific HLA-DR predictions using a novel concurrent alignment and weight optimization training procedure. *Immunome Res* 6: 9; Nielsen M, Lund O. 2009. NN-align. An artificial neural network-based alignment algorithm for MHC class II peptide binding prediction. *BMC Bioinformatics* 10: 296). 144 peptides for E6, 84 peptides for E7, 351 peptides for E2 and 69 peptides for E5 binding to eleven different HLA-DR molecules were identified. To select promiscuous CD4+ T cell epitopes, for each protein, the 15-mer candidate peptides were ranked according to their binding affinity to multiple HLA-DR alleles, excluding those harboring more than two cystein residues to minimize complexities resulting from intramolecular or intermolecular disulfide bond formation. Six candidate peptides of E6 and E7 as well as eleven and eight candidate peptides from E2 and E5, respectively, which were predicted as binders by any one of the prediction algorithms and bound to at least 5 different HLA-DR molecules (Table 1) were synthesized and used for subsequent assays. As shown in Table 1, predictions were not completely consistent between the two algorithms.

Evaluation of HPV16 Peptide-Specific T Cell Immunity in Healthy Subjects

To investigate whether the predicted candidate peptides were able to stimulate T cells from a cohort of healthy donors, the inventors used a 6-day IFN-γ ELISPOT assay. Frequencies of reactive T cells to each candidate peptide and the number of positive responders are reported for E6- and E7-derived peptides in Table 2, and for E2- and E5-derived peptides in Table 3. T cells isolated from the majority of healthy subjects showed reactivity against one or more of the HPV16-derived candidate peptides, after a single round of in vitro stimulation. The peptides E6/54-68 (30% response rate of tested healthy subjects), E6/74-88 (45%), E7/12-26 (40%), E7/64-78 (40%), E2/76-90 (30%), E2/99-113 (35%), E2/156-170 (40%), E5/33-48 (50%), E5/54-69 (55%), and E5/67-81 (60%) were found to be the most potent epitopes in this cohort of individuals expressing a wide variety of HLA-DR molecules. To further characterize the immune potency of these ten selected peptides, PBMC from an independent set of 13 healthy subjects were analyzed in a 12 day culture expansion of preexisting memory T cells. Using this approach, even higher frequencies of IFN-γ producing T cells against the selected HPV16-derived peptides could be observed (FIG. 1). For each peptide a high response rate was observed, with 92% cumulative response rate (against all selected peptides) in the whole cohort of tested healthy donors. The five peptides showing the highest response rates and average spot numbers (E2/156-170, E5/33-48, E6/74-88, E7/12-26 and E7/64-78) were chosen for further analysis.

Peptide Reactivity is Abrogated in the Presence of Anti-HLA-DR Antibodies

To determine whether the selected HPV16-derived peptides were HLA-DR-restricted, PBMC were incubated with the HLA-DR blocking antibody L243 before peptide exposure and then subjected to IFN-γ ELISPOT assay. Similarly, PBMC cultures were incubated with the panspecific HLA class I blocking antibody W6/32. Two subjects were analyzed in this assay. As shown in FIG. 2, peptide-specific T cell responses were abrogated in all cases under anti-HLA-DR antibody treatment, indicating that the epitopes are truly HLA-DR-restricted. However, the reactivity of the E5/33-48 peptide was partially reduced when PBMC from subject HD54 were cultured with the anti-panHLA-I antibody W6/32 (FIG. 2A). This was not observed with this peptide with PBMC from HD55 (FIG. 2B). Further, blocking activity of the anti-panHLA-I antibody was found in PBMC cultures of both subjects stimulated with E7/64-78 peptide, and with E6/74-88-stimulated PBMC from subject HD55. These results indicate that the 15-mer peptides E5/33-48, E6/74-88 and E7/64-78 are harboring epitopes restricted by some HLA class I molecules.

The Induced HPV16 Peptide-Specific T Cell Immunity is CD4+ T Cell-Mediated

To verify whether the observed peptide-specific T cell responses are indeed mediated by CD4+ T cells, the inventors tested the five selected peptides in an IFN-γ intracellular cytokine secretion (ICS) assay in 7 healthy subjects. Even if HPV16 peptide-specific T cell reactivities detected by this assay were generally low, a predominance of CD4+ T cells compared to CD8+ T cells could be observed (FIG. 3A). This difference was found to be significant for E2/156-170 (P=0.013), E6/74-88 (P=0.01), E7/64-78 (P=0.05), but not for E5/33-48 (P=0.14) and E7/12-26 (P=0.10). This approach allowed us to assess T cell subsets taking part in immune response against the selected HPV16 peptides. However, the inventors conclude that the ICS method is not sensitive enough to assess preexisting HPV responses in healthy subjects.

To independently verify these findings with another method, PBMC were depleted of CD4+ T cells (and, if sufficient PBMC were available from a donor, also of CD8+ T cells) prior to in vitro peptide stimulation and subjected to ELISPOT analysis. The same five selected peptides were analyzed in an independent set of twelve subjects for this assay. CD4+ T cell-depletion resulted in significant loss of peptide reactivity (P≤0.05) in the majority of tested subjects (FIG. 3B), again showing that the peptide-specific immune responses are mediated by CD4+ T cells. CD8+ T cell-depletion did not affect peptide-specific IFN-γ production (FIG. 3C). However, reactivity of the E7/64-78 peptide was not abolished in CD4+ T cell-depleted PBMC from subject HD24, indicating some CD8+ T cell reactivity to this peptide in this donor. Taken together, these data provide strong evidence that the selected HPV16-derived peptides are able to induce CD4+ T cell-mediated immunity.

Peptide-Specific CD4+ T Cells have a Th1 Phenotype

In order to investigate the functional properties of peptide-specific CD4+ T cells, the inventors assessed the Th1/Th2 cytokine profile. Analysis of supernatants of T cell cultures from HD23 for presence of IFN-γ, TNF-α, GM-CSF, IL-4, IL-5 and IL-2 showed predominant secretion of Th1 effector cytokines in response to the selected HPV16-derived peptides (FIG. 4A). High levels of IFN-γ, TNF-α (except for peptide E5/33-48) and GM-CSF were detected, whereas only weak or no production of IL-4 and IL-5 was observed. Interestingly, IL-2 was not detected in these T cell cultures, which is probably due to its consumption by the proliferating T cells (this cytokine was not provided during the PBMC culture). Furthermore, the inventors tested in five subjects whether the observed CD4+ T cell-mediated immunity in the peptide-stimulated T cell cultures contains regulatory T cells (Treg). To do so, the inventors determined the frequency of peptide-specific CD4+/CD25+/FoxP3+ T cells after 12 days of peptide stimulation. Only minor populations of peptide-specific CD4+/CD25+/FoxP3+ T cells were found in PBMC cultures after stimulation with the selected HPV16-derived peptides (FIG. 4B, representative results of one donor—HD23—are shown).

TABLE 1

Candidate pan-HLA-DR binding peptides derived from the HPV16 E2, E5, E6 and E7 proteins.

| Peptide (protein/ position) | Sequence (SEQ ID No.) | SYFPEITHI High scoring HLA-DR alleles[a] | SYFPEITHI Other scoring HLA-DR alleles[b] | NetMHCII High affinity binding HLA-DR alleles[c] | NetMHCII Other binding HLA-DR alleles[d] |
|---|---|---|---|---|---|
| E6/16-30 | PRKLPQLCTELQTTI (SEQ ID No. 1) | DRB1*01, *04 | DRB1*03, *07, *11, *15 | | DRB1*01, *04, DRB4 |
| E6/42-56 | QQLLRREVYDFAFRD (SEQ ID No. 2) | DRB1*04 | DRB1*01, *03, *07, *11, *15 | | DRB1*01, *03, *04, *15, DRB3, DRB4, DRB5 |
| E6/54-68 | FRDLCIVYRDGNPYA (SEQ ID No. 3) | DRB1*04, *11 | DRB1*01, *03, *15 | | DRB1*01, *04, *11, *13, *15, DRB3, DRB5 |
| E6/74-88 | LKFYSKISEYRHYCY (SEQ ID No. 4) | DRB1*07 | DRB1*01, *04, *11 | DRB1*01, *15, DRB5 | DRB1*04, *07, *09, *11 |
| E6/92-106 | GTTLEQQYNKPLCDL (SEQ ID No. 5) | DRB1*01, *03, *04, *07 | DRB1*15 | | DRB1*01, *13, DRB4 |
| E6/129-143 | KQRFHNIRGRWTGRC (SEQ ID No. 6) | DRB1*01, *04 | DRB1*07, *11, *15 | | DRB1*01, *04, *07, *09, *11, *15, DRB5 |
| E7/12-26 | MLDLQPETTDLYCYE (SEQ ID No. 7) | DRB1*03, *04, *07 | DRB1*01, *15 | | DRB1*01, *03 |
| E7/63-77 | STLRLCVQSTHVDIR (SEQ ID No. 8) | DRB1*01 | DRB1*04, *07 | DRB1*01, *07, DRB4 | DRB1*03, *04, *09, *11, *13, *15, DRB5 |
| E7/64-78 | TLRLCVQSTHVDIRT (SEQ ID No. 9) | DRB1*01 | DRB1*03, *04, *07, *15 | DRB1*01, *07, DRB4 | DRB1*03, *04, *09, *11, *13, *15, DRB5 |
| E7/71-85 | STHVDIRTLEDLLMG (SEQ ID No. 10) | | DRB1*01, *03, *07, *15 | | DRB1*01, *03, *04, *07, DRB4 |
| E7/73-87 | HVDIRTLEDLLMGTL (SEQ ID No. 11) | DRB1*01, *04, *07, *15 | DRB1*03, *11 | DRB1*01 | DRB1*03, *04, DRB4 |

TABLE 1-continued

Candidate pan-HLA-DR binding peptides derived from the HPV16 E2, E5, E6 and E7 proteins.

| Peptide (protein/ position) | Sequence (SEQ ID No.) | SYFPEITHI High scoring HLA-DR alleles[a] | SYFPEITHI Other scoring HLA-DR alleles[b] | NetMHCII High affinity binding HLA-DR alleles[c] | NetMHCII Other binding HLA-DR alleles[d] |
|---|---|---|---|---|---|
| E7/76-90 | IRTLEDLLMGTLGIV (SEQ ID No. 12) | DRB1*01, *04 | DRB1*03, *07, *11, *15 | DRB1*01 | DRB1*04, *07, DRB4 |
| E2/27-42 | RDHIDYWKHMRLECA (SEQ ID No. 13) | DRB1*04, *15 | DRB1*01, *03, *07, *11 | DRB1*11 | DRB1*01, *07, *15, DRB4 |
| E2/51-65 | FKHINHQVVPTLAVS (SEQ ID No. 14) | DRB1*01 | DRB1*03, *04, *07, *15 | DRB1*01, *07 | DRB1*04, *09, *11, *13, *15, DRB4, DRB5 |
| E2/59-73 | VPTLAVSKNKALQAI (SEQ ID No. 15) | DRB1*03, *04, *07 | DRB1*01, *15 | DRB1*01, *13 | DRB1*03, *07, *09, *11, DRB4, DRB5 |
| E2/76-90 | QLTLETIYNSQYSNE (SEQ ID No. 16) | DRB1*03, *04, *07 | DRB1*01, *11, *15 | | DRB1*01, *04, *15 |
| E2/99-113 | LEVYLTAPTGCIKKH (SEQ ID No. 17) | DRB1*01, *04, *07 | DRB1*11 | DRB1*01, *07, DRB5 | DRB1*04, *09, *11, *15, DRB3 |
| E2/156-170 | GLYYVHEGIRTYFVQ (SEQ ID No. 18) | | DRB1*01, *03, *04, *07, *11 | DRB1*01, *07, *15, DRB3, DRB5 | DRB1*03, *04, *09, *11, DRB4 |
| E2/208-223 | PEIIRQHLANHPAAT (SEQ ID No. 19) | DRB1*01 | DRB1*03, *04, *11, *15 | DRB1*01, DRB4 | DRB1*04, *07, *09, *11, *13, *15, DRB5 |
| E2/267-282 | ILTAFNSSHKGRINC (SEQ ID No. 20) | | | DRB1*07, *09, DRB5 | DRB1*01, *04, *11, *13, *15 |
| E2/288-302 | IVHLKGDANTLKCLR (SEQ ID No. 21) | DRB1*03, *04 | DRB1*01, *07, *15 | DRB1*03 | DRB1*01, *04, DRB3, DRB5 |
| E2/300-314 | CLRYRFKKHCTLYTA (SEQ ID No. 22) | DRB1*01 | DRB1*03, *04, *07, *11 | DRB1*01, *07, *11, *15 | DRB1*04, *09, DRB3, DRB5 |
| E2/344-359 | DQFLSQVKIPKTITV (SEQ ID No. 23) | DRB1*04 | DRB1*01, *03, *11, *15 | DRB1*01, *11, DRB5 | DRB1*04, *07, *09, *13, *15, DRB4 |
| E5/1-15 | MTNLDTASTTLLACF (SEQ ID No. 24) | DRB1*01, *03, *04, *07 | DRB1*15 | DRB1*01, *07 | DRB1*03, *04, *09, *13 |
| E5/30-45 | RPLLLSVSTYTSLIL (SEQ ID No. 25) | DRB1*01, *04 | DRB1*03, *07, *11, *15 | DRB1*01, *04, *07, *15 | DRB1*03, *09, *11, *13, DRB4, DRB5 |
| E5/33-48 | LLSVSTYTSLILLVL (SEQ ID No. 26) | DRB1*01, *04, *07, *15 | DRB1*03 | DRB1*01, *07, *15 | DRB1*04, *09, *11, |
| E5/45-60 | LVLVLWITAASAFRC (SEQ ID No. 27) | DRB1*01, *04 | DRB1*03, *07, *11, *15 | DRB1*01, *07, *09, DRB5 | DRB1*04, *11, *13, *15, DRB3 |

TABLE 1-continued

Candidate pan-HLA-DR binding peptides derived from the HPV16 E2, E5, E6 and E7 proteins.

| Peptide (protein/ position) | Sequence (SEQ ID No.) | SYFPEITHI High scoring HLA-DR alleles[a] | Other scoring HLA-DR alleles[b] | NetMHCII High affinity binding HLA-DR alleles[c] | Other binding HLA-DR alleles[d] |
|---|---|---|---|---|---|
| E5/54-69 | ASAFRCFIVYIVFVY (SEQ ID No. 28) | DRB1*01, *04, *15 | DRB1*07, *11 | | DRB1*01, *11, *15 |
| E5/60-74 | FIVYIVFVYIPLFLI (SEQ ID No. 29) | DRB1*04, *15 | DRB1*01, *07, *11 | | DRB1*01, *07, *15, DRB3 |
| E5/67-81 | VYIPLFLIHTHARFL (SEQ ID No. 30) | DRB1*11 | DRB1*01, *04 | DRB1*01, *04, *07, *11, *13, *15, DRB5 | DRB1*03, *09, DRB3, DRB4 |
| E5/69-84 | IPLFLIHTHARFLIT (SEQ ID No. 31) | DRB1*01, *11 | DRB1*03, *04, *07 | DRB1*01, *03, *04, *07, *11, *13, *15, DRB5 | DRB1*09, DRB3, DRB4 |

[a]Threshold for good binding peptides: score ≥20.
[b]Threshold for other binding peptides: score 19 ≤ 10.
[c]Threshold for good binding peptides: $IC_{50}$ ≤ 60 nM.
[d]Threshold for other binding peptides $IC_{50}$ 60 ≤ 1000 nM.

TABLE 2

HPV16 E6- and E7-specific T-cell responses in healthy donors as measured by IFN-γ ELISPOT

| Donor | HLA-DRB1 genotype | HPV16 E6 peptides | | | | | | HPV16 E7 peptides | | | | | |
|---|---|---|---|---|---|---|---|---|---|---|---|---|---|
| | | E6/16-30 | E6/42-56 | E6/54-68 | E6/74-88 | E6/92-106 | E6/129-143 | E7/12-26 | E7/63-77 | E7/64-78 | E7/71-85 | E7/73-87 | E7/76-90 |
| HD1 | *04, — | 55[a] | 12 | 25 | 35 | — | 88 | 128 | 58 | 98 | 88 | 82 | 192 |
| HD2 | *03, *11 | — | 27 | — | — | — | 13 | 13 | — | — | — | — | — |
| HD3 | *03, *04 | 187 | 260 | 233 | 183 | 63 | 113 | 80 | 80 | 133 | 177 | 180 | 323 |
| HD4 | *04, *16 | 17 | — | 30 | — | 7 | 7 | — | 27 | — | — | — | — |
| HD5 | *01, *16 | 2 | 288 | 392 | 528 | — | 122 | 28 | 205 | 185 | — | — | — |
| HD6 | *03, *13 | — | 50 | 130 | 220 | 7 | 97 | 567 | 3 | 63 | 13 | 63 | 20 |
| HD7 | *08, *11 | — | — | — | — | 7 | — | 3 | 3 | — | 60 | 7 | — |
| HD8 | *13, — | — | — | — | — | — | — | — | 63 | — | — | — | — |
| HD9 | *01, *07 | 2 | 2 | 2 | 35 | 18 | 2 | — | 18 | 5 | — | — | — |
| HD10 | *04, *13 | 85 | 15 | 2 | 142 | 18 | 45 | 68 | 78 | 245 | 58 | 115 | 48 |
| HD11 | *01, *04 | 250 | 163 | 77 | 73 | 70 | 207 | 347 | 113 | 133 | 43 | — | 117 |
| HD12 | *03, *11 | 263 | 73 | 250 | 393 | 243 | 83 | 223 | 447 | 270 | 350 | 190 | 223 |
| HD13 | *11, *14 | 125 | 105 | 108 | 222 | 168 | 135 | 258 | 68 | 265 | 15 | 72 | 38 |
| HD14 | *07, *13 | — | 143 | 33 | 213 | 87 | 37 | 190 | 140 | 227 | 127 | 40 | 113 |
| HD15 | *01, *08 | 20 | 37 | 63 | 40 | 13 | 10 | 63 | 87 | 130 | 237 | 67 | 73 |
| HD16 | *07, *13 | 45 | 195 | 18 | 22 | 45 | 25 | 192 | 172 | 98 | 328 | 72 | 22 |
| HD17 | *01, *15 | 142 | 282 | 132 | 332 | 235 | 458 | 342 | 242 | 812 | 438 | 298 | 278 |
| HD18 | *08, *13 | 5 | 162 | — | 85 | — | 5 | 258 | 228 | 215 | — | 48 | 98 |
| HD19 | *01, *15 | 518 | 162 | 362 | 168 | 108 | — | 355 | 315 | 418 | 215 | 202 | 82 |
| HD20 | *07, *15 | 175 | 85 | 75 | 95 | 115 | 118 | 318 | 128 | 108 | 192 | 165 | 95 |
| Positive responders (%) | | 5 (25%) | 5 (25%) | 6 (30%) | 9 (45%) | 2 (10%) | 5 (25%) | 8 (40%) | 5 (25%) | 8 (40%) | 6 (30%) | 4 (20%) | 3 (15%) |

[a]Number of peptide-specific memory T cells per $10^6$ PBMC. Data represent the mean result from triplicate wells after background subtraction. A dash indicates that no specific T cell reactivity was detected. Responses are considered positive (bold) if they were at least twofold higher than the background.

TABLE 3

HPV16 E2- and E5-specific T-cell responses in healthy donors as measured by IFN-γ ELISPOT

| Donor | HLA-DRB1 geno-type | HPV16 E2 peptides | | | | | | | | | |
|---|---|---|---|---|---|---|---|---|---|---|---|
| | | E2/27-42 | E2/51-65 | E2/59-73 | E2/76-90 | E2/99-113 | E2/156-170 | E2/208-223 | E2/267-282 | E2/288-302 | E2/300-314 |
| HD21 | *7, *13 | 123[a] | 7 | 47 | 50 | 147 | 13 | 13 | 7 | 13 | 7 |
| HD22 | *04, *15 | — | 3 | 3 | 7 | 27 | 7 | — | 10 | 3 | — |
| HD23 | *11, *13 | — | — | — | — | — | 10 | — | 13 | 20 | 13 |
| HD24 | *09, *12 | 3 | 7 | 7 | — | 20 | 10 | 17 | 10 | 3 | 10 |
| HD25 | *03, *15 | 170 | — | — | 3 | 110 | — | — | — | — | — |
| HD26 | *04, *16 | — | — | — | — | 10 | 23 | 17 | — | — | 30 |
| HD27 | *01, *11 | 10 | 57 | 87 | 60 | 133 | 53 | 40 | 87 | 3 | 77 |
| HD28 | *11, *15 | 27 | 27 | — | 223 | — | 493 | 73 | 17 | 57 | 7 |
| HD29 | *04, *16 | 17 | 23 | — | 57 | 33 | 87 | 3 | 13 | — | 143 |
| HD30 | *07, *11 | — | 10 | — | — | 3 | 3 | 3 | — | — | 7 |
| HD31 | *07, *11 | — | — | — | 3 | 50 | 77 | 47 | 23 | 27 | 20 |
| HD32 | *01, *16 | — | — | 3 | 7 | 40 | 40 | 7 | 3 | 3 | — |
| HD33 | *04, *07 | 150 | 40 | 173 | 120 | 73 | 617 | 93 | — | 270 | 123 |
| HD34 | *04, — | — | — | 13 | 3 | — | — | 7 | 10 | — | — |
| HD35 | *11, — | 3 | 17 | 33 | 20 | — | — | 7 | — | 7 | 17 |
| HD36 | *04, — | 47 | — | — | — | 47 | 403 | — | — | 13 | 127 |
| HD37 | *04, *07 | 47 | 10 | 167 | 307 | 83 | 167 | 17 | 40 | 77 | 123 |
| HD38 | *13, *15 | 100 | 10 | 30 | 33 | 350 | 47 | 53 | 23 | 7 | 27 |
| HD39 | *04, *13 | 10 | 17 | 27 | 33 | 13 | 13 | — | 3 | — | 83 |
| HD40 | *03, *04 | — | 10 | 37 | 17 | 3 | 23 | — | 3 | — | 20 |
| Positive responders (%) | | 3 (15%) | 2 (10%) | 4 (20%) | 6 (30%) | 7 (35%) | 8 (40%) | 3 (15%) | 2 (10%) | 2 (10%) | 5 (25%) |

| Donor | HLA-DRB1 geno-type | HPV16 E2 peptides | HPV16 E5 peptides | | | | | | | |
|---|---|---|---|---|---|---|---|---|---|---|
| | | E2/344-359 | E5/1-15 | E5/30-45 | E5/33-48 | E5/45-60 | E5/54-69 | E5/60-74 | E5/67-81 | E5/69-84 |
| HD21 | *07, *13 | 40 | 7 | — | 67 | 20 | 153 | 97 | 40 | 3 |
| HD22 | *04, *15 | 3 | 3 | 3 | 17 | 13 | 7 | 220 | 7 | 10 |
| HD23 | *11, *13 | 23 | — | 3 | — | 43 | 193 | 200 | — | 3 |
| HD24 | *09, *12 | — | — | 7 | 23 | — | 17 | 433 | 3 | 3 |
| HD25 | *03, *15 | — | 13 | 70 | 207 | 43 | 7 | 17 | 27 | 23 |
| HD26 | *04, *16 | 13 | — | 7 | — | 77 | 50 | 33 | 100 | — |
| HD27 | *01, *11 | 73 | 223 | 247 | 73 | 97 | 140 | 200 | 133 | 13 |
| HD28 | *11, *15 | 10 | 270 | 60 | 37 | 250 | 143 | 147 | 180 | 63 |
| HD29 | *04, *16 | 7 | 3 | — | 13 | — | 10 | 40 | 60 | 113 |
| HD30 | *07, *11 | 13 | — | — | — | 3 | 7 | 27 | 13 | — |
| HD31 | *07, *11 | 3 | 13 | 73 | 7 | 3 | 80 | 107 | — | — |
| HD32 | *01, *16 | 10 | 30 | 47 | — | — | 33 | 13 | — | 3 |
| HD33 | *04, *07 | 103 | 283 | 130 | 500 | 407 | 367 | 27 | 73 | 110 |
| HD34 | *04, — | 13 | — | 30 | 30 | 7 | 40 | 43 | — | — |
| HD35 | *11, — | 10 | 10 | 10 | 170 | 20 | 157 | 207 | 50 | 20 |
| HD36 | *04, — | 123 | — | 80 | 77 | — | 27 | 40 | 17 | — |
| HD37 | *04, *07 | 43 | — | 183 | 50 | 297 | 80 | 127 | 93 | 17 |
| HD38 | *13, *15 | 37 | 53 | 173 | 160 | 247 | 280 | 183 | 227 | 50 |
| HD39 | *04, *13 | 107 | 3 | 10 | 27 | 10 | 73 | 47 | 23 | — |
| HD40 | *03, *04 | 3 | 30 | 17 | 20 | 20 | 53 | 27 | 20 | 23 |
| Positive responders (%) | | 3 (15%) | 4 (20%) | 5 (25%) | 10 (50%) | 6 (30%) | 11 (55%) | 12 (60%) | 7 (35%) | 3 (15%) |

[a]Number of peptide-specific memory T cells per $10^6$ PBMC. Data represent the mean result from triplicate wells after background subtraction. A dash indicates that no specific T cell reactivity was detected. Responses are considered positive (bold) if they were at least twofold higher than the background.

TABLE 4

Comparison of the predicted HLA-DRB1 alleles with the experimentally tested HLA-DRB1 molecules presenting selected HPV16-derived peptides.

| Peptide (protein/ position) | HLA-DRB1 molecules predicted to bind a given peptide | HLA-DRB1 genotype of responders |
| --- | --- | --- |
| E6/54-68 | *01, *03, 04, 11, *13, *15 | *03/*04; *01/*16; *03/*13; *03/*11; *01/*08; *01/*15 |
| E6/74-88 | *01, *04, 07, *09, *11, 15 | *03/*04; *01/*16; *03/*13; *01/*07; *04/*13; *03/*11; *07/*13; *01/*08; *01/*15 |
| E7/12-26 | *01, 03, 04, 07, *15 | *03/*04; *03/*13; *01/*04; *03/*11; *01/*08; *01/*15; *07/*15 |
| E7/64-78 | *01, *03, *04, 07, *09, *11, *13, *15 | *03/*04; *03/*13; *04/*13; *03/*11; *07/*13; *01/*08; *01/*15 |
| E7/71-85 | *01, *03, *04, *07, *15 | *03/*04; *08/*11; *03/*11; *01/*08; *07/*13; *01/*15 |
| E2/76-90 | *01, 03, *04, 07, *11, *15 | *07/*13; *01/*11; *11/*15; *04/*16; *04/*07; *04/*13 |
| E2/99-113 | *01, *04, 07, *09, *11, *15 | *07/*13; *09/*12; *03/*15; *01/*11; *04/*07; *13/*15 |
| E2/156-170 | *01, *03, *04, 07, *09, *11, 15 | *09/*12; *01/*11; *11/*15; *04/*16; *04/*07; *04/—; *13/*15 |
| E5/33-48 | *01, *03, 04, 07, *09, *11, 15 | *07/*13; *09/*12; *03/*15; *01/*11; *04/*07; *13/*15; *04/*13 |
| E5/45-60 | *01, *03, 04, 07, *09, *11, *13, 15 | *11/*13; *01/*11; *11/*15; *04/*07; *13/*15 |
| E5/54-69 | *01, 04, *07, *11, 15 | *07/*13; *11/*13; *09/*12; *01/*11; *11/*15; *04/*07; *11/—; *13/*15; *04/*13; *03/*04 |
| E5/60-74 | *01, 04, *07, *11, 15 | *07/*13; *04/*15; *11/*13; *09/*12; *01/*11; *11/*15; *07/*11; *04/—; *11/—; *04/*07; *13/*15; *04/*13 |
| E5/67-81 | *01, *03, 04, 07, *09, *11, *13, *15 | *04/*16; *01/*11; *11/*15; *04/*07; *13/*15; *04/*13 |

Peptides in bold: selected for detailed analysis.
HLA-DRB1 molecules in bold: predicted as high affinity binding or scoring.

The invention claimed is:

1. A method for treating HPV infection, HPV-related premalignancies and/or malignancies, wherein said method comprises administering, to a patient in need of said treatment, a pharmaceutical composition comprising a peptide comprising a sequence according to SEQ ID NO: 4 or a variant thereof that is at least 90% homologous to SEQ ID NO: 4, wherein said peptide, or one or more parts thereof, has the ability to bind to a molecule of the human major histocompatibility complex (MHC) class-II or -I, and wherein said peptide has a length of 15 to 20 amino acids.

2. The method for treating HPV infection, HPV-related premalignancies and/or malignancies according to claim 1, wherein said treatment is MHC-I and/or MHC-II peptide presentation dependent.

3. The method for treating HPV infection, HPV-related premalignancies and/or malignancies according to claim 1, wherein the pharmaceutical composition further comprises at least one additional peptide consisting of an amino acid sequence selected from the group of SEQ ID NOs: 26, 9, 7, and 18.

4. The method for treating HPV infection, HPV-related premalignancies and/or malignancies according to claim 1, wherein the peptide has the ability to bind to a molecule of the human MHC class-II.

5. The method for treating HPV infection, HPV-related premalignancies and/or malignancies according to claim 1, wherein the peptide has the ability to bind to at least three MHC II molecules.

6. The method for treating HPV infection, HPV-related premalignancies and/or malignancies according to claim 1, wherein the peptide has a length of 15 amino acids.

7. The method for treating HPV infection, HPV-related premalignancies and/or malignancies according to claim 1, wherein the peptide consists of a sequence according to SEQ ID NO: 4.

* * * * *

UNITED STATES PATENT AND TRADEMARK OFFICE
CERTIFICATE OF CORRECTION

PATENT NO. : 9,932,371 B2  
APPLICATION NO. : 15/104165  
DATED : April 3, 2018  
INVENTOR(S) : Agnieszka Grabowska and Angelika Riemer Page 1 of 1

It is certified that error appears in the above-identified patent and that said Letters Patent is hereby corrected as shown below:

In the Specification

Column 7,
Lines 64-65, "-CH$_2$-NH, -CH$_2$CH$_2$-," should read -- -CH$_2$-NH, -CH$_2$S-, -CH$_2$CH$_2$-, --.

Column 27,
Line 56, "HD35 *11, - 10 10 10…" should read -- HD35 *11, -… 30 10 10… --.

Signed and Sealed this  
Thirtieth Day of October, 2018

Andrei Iancu  
*Director of the United States Patent and Trademark Office*

SEQUENCE LISTING

<160> NUMBER OF SEQ ID NOS: 31

<210> SEQ ID NO 1
<211> LENGTH: 15
<212> TYPE: PRT
<213> ORGANISM: Human papillomavirus type 16

<400> SEQUENCE: 1

Pro Arg Lys Leu Pro Gln Leu Cys Thr Glu Leu Gln Thr Thr Ile
1               5                   10                  15

<210> SEQ ID NO 2
<211> LENGTH: 15
<212> TYPE: PRT
<213> ORGANISM: Human papillomavirus type 16

<400> SEQUENCE: 2

Gln Gln Leu Leu Arg Arg Glu Val Tyr Asp Phe Ala Phe Arg Asp
1               5                   10                  15

<210> SEQ ID NO 3
<211> LENGTH: 15
<212> TYPE: PRT
<213> ORGANISM: Human papillomavirus type 16

<400> SEQUENCE: 3

Phe Arg Asp Leu Cys Ile Val Tyr Arg Asp Gly Asn Pro Tyr Ala
1               5                   10                  15

<210> SEQ ID NO 4
<211> LENGTH: 15
<212> TYPE: PRT
<213> ORGANISM: Human papillomavirus type 16

<400> SEQUENCE: 4

-continued

```
Leu Lys Phe Tyr Ser Lys Ile Ser Glu Tyr Arg His Tyr Cys Tyr
1               5                   10                  15

<210> SEQ ID NO 5
<211> LENGTH: 15
<212> TYPE: PRT
<213> ORGANISM: Human papillomavirus type 16

<400> SEQUENCE: 5

Gly Thr Thr Leu Glu Gln Gln Tyr Asn Lys Pro Leu Cys Asp Leu
1               5                   10                  15

<210> SEQ ID NO 6
<211> LENGTH: 15
<212> TYPE: PRT
<213> ORGANISM: Human papillomavirus type 16

<400> SEQUENCE: 6

Lys Gln Arg Phe His Asn Ile Arg Gly Arg Trp Thr Gly Arg Cys
1               5                   10                  15

<210> SEQ ID NO 7
<211> LENGTH: 15
<212> TYPE: PRT
<213> ORGANISM: Human papillomavirus type 16

<400> SEQUENCE: 7

Met Leu Asp Leu Gln Pro Glu Thr Thr Asp Leu Tyr Cys Tyr Glu
1               5                   10                  15

<210> SEQ ID NO 8
<211> LENGTH: 15
<212> TYPE: PRT
<213> ORGANISM: Human papillomavirus type 16

<400> SEQUENCE: 8

Ser Thr Leu Arg Leu Cys Val Gln Ser Thr His Val Asp Ile Arg
1               5                   10                  15

<210> SEQ ID NO 9
<211> LENGTH: 15
<212> TYPE: PRT
<213> ORGANISM: Human papillomavirus type 16

<400> SEQUENCE: 9

Thr Leu Arg Leu Cys Val Gln Ser Thr His Val Asp Ile Arg Thr
1               5                   10                  15

<210> SEQ ID NO 10
<211> LENGTH: 15
<212> TYPE: PRT
<213> ORGANISM: Human papillomavirus type 16

<400> SEQUENCE: 10

Ser Thr His Val Asp Ile Arg Thr Leu Glu Asp Leu Leu Met Gly
1               5                   10                  15

<210> SEQ ID NO 11
<211> LENGTH: 15
<212> TYPE: PRT
<213> ORGANISM: Human papillomavirus type 16

<400> SEQUENCE: 11

His Val Asp Ile Arg Thr Leu Glu Asp Leu Leu Met Gly Thr Leu
1               5                   10                  15
```

<210> SEQ ID NO 12
<211> LENGTH: 15
<212> TYPE: PRT
<213> ORGANISM: Human papillomavirus type 16

<400> SEQUENCE: 12

Ile Arg Thr Leu Glu Asp Leu Leu Met Gly Thr Leu Gly Ile Val
1               5                   10                  15

<210> SEQ ID NO 13
<211> LENGTH: 15
<212> TYPE: PRT
<213> ORGANISM: Human papillomavirus type 16

<400> SEQUENCE: 13

Arg Asp His Ile Asp Tyr Trp Lys His Met Arg Leu Glu Cys Ala
1               5                   10                  15

<210> SEQ ID NO 14
<211> LENGTH: 15
<212> TYPE: PRT
<213> ORGANISM: Human papillomavirus type 16

<400> SEQUENCE: 14

Phe Lys His Ile Asn His Gln Val Val Pro Thr Leu Ala Val Ser
1               5                   10                  15

<210> SEQ ID NO 15
<211> LENGTH: 15
<212> TYPE: PRT
<213> ORGANISM: Human papillomavirus type 16

<400> SEQUENCE: 15

Val Pro Thr Leu Ala Val Ser Lys Asn Lys Ala Leu Gln Ala Ile
1               5                   10                  15

<210> SEQ ID NO 16
<211> LENGTH: 15
<212> TYPE: PRT
<213> ORGANISM: Human papillomavirus type 16

<400> SEQUENCE: 16

Gln Leu Thr Leu Glu Thr Ile Tyr Asn Ser Gln Tyr Ser Asn Glu
1               5                   10                  15

<210> SEQ ID NO 17
<211> LENGTH: 15
<212> TYPE: PRT
<213> ORGANISM: Human papillomavirus type 16

<400> SEQUENCE: 17

Leu Glu Val Tyr Leu Thr Ala Pro Thr Gly Cys Ile Lys Lys His
1               5                   10                  15

<210> SEQ ID NO 18
<211> LENGTH: 15
<212> TYPE: PRT
<213> ORGANISM: Human papillomavirus type 16

<400> SEQUENCE: 18

Gly Leu Tyr Tyr Val His Glu Gly Ile Arg Thr Tyr Phe Val Gln
1               5                   10                  15

```
<210> SEQ ID NO 19
<211> LENGTH: 15
<212> TYPE: PRT
<213> ORGANISM: Human papillomavirus type 16

<400> SEQUENCE: 19

Pro Glu Ile Ile Arg Gln His Leu Ala Asn His Pro Ala Ala Thr
1               5                   10                  15

<210> SEQ ID NO 20
<211> LENGTH: 15
<212> TYPE: PRT
<213> ORGANISM: Human papillomavirus type 16

<400> SEQUENCE: 20

Ile Leu Thr Ala Phe Asn Ser Ser His Lys Gly Arg Ile Asn Cys
1               5                   10                  15

<210> SEQ ID NO 21
<211> LENGTH: 15
<212> TYPE: PRT
<213> ORGANISM: Human papillomavirus type 16

<400> SEQUENCE: 21

Ile Val His Leu Lys Gly Asp Ala Asn Thr Leu Lys Cys Leu Arg
1               5                   10                  15

<210> SEQ ID NO 22
<211> LENGTH: 15
<212> TYPE: PRT
<213> ORGANISM: Human papillomavirus type 16

<400> SEQUENCE: 22

Cys Leu Arg Tyr Arg Phe Lys Lys His Cys Thr Leu Tyr Thr Ala
1               5                   10                  15

<210> SEQ ID NO 23
<211> LENGTH: 15
<212> TYPE: PRT
<213> ORGANISM: Human papillomavirus type 16

<400> SEQUENCE: 23

Asp Gln Phe Leu Ser Gln Val Lys Ile Pro Lys Thr Ile Thr Val
1               5                   10                  15

<210> SEQ ID NO 24
<211> LENGTH: 15
<212> TYPE: PRT
<213> ORGANISM: Human papillomavirus type 16

<400> SEQUENCE: 24

Met Thr Asn Leu Asp Thr Ala Ser Thr Thr Leu Leu Ala Cys Phe
1               5                   10                  15

<210> SEQ ID NO 25
<211> LENGTH: 15
<212> TYPE: PRT
<213> ORGANISM: Human papillomavirus type 16

<400> SEQUENCE: 25

Arg Pro Leu Leu Leu Ser Val Ser Thr Tyr Thr Ser Leu Ile Leu
1               5                   10                  15

<210> SEQ ID NO 26
<211> LENGTH: 15
```

```
<212> TYPE: PRT
<213> ORGANISM: Human papillomavirus type 16

<400> SEQUENCE: 26

Leu Leu Ser Val Ser Thr Tyr Thr Ser Leu Ile Leu Leu Val Leu
1               5                   10                  15

<210> SEQ ID NO 27
<211> LENGTH: 15
<212> TYPE: PRT
<213> ORGANISM: Human papillomavirus type 16

<400> SEQUENCE: 27

Leu Val Leu Val Leu Trp Ile Thr Ala Ala Ser Ala Phe Arg Cys
1               5                   10                  15

<210> SEQ ID NO 28
<211> LENGTH: 15
<212> TYPE: PRT
<213> ORGANISM: Human papillomavirus type 16

<400> SEQUENCE: 28

Ala Ser Ala Phe Arg Cys Phe Ile Val Tyr Ile Val Phe Val Tyr
1               5                   10                  15

<210> SEQ ID NO 29
<211> LENGTH: 15
<212> TYPE: PRT
<213> ORGANISM: Human papillomavirus type 16

<400> SEQUENCE: 29

Phe Ile Val Tyr Ile Val Phe Val Tyr Ile Pro Leu Phe Leu Ile
1               5                   10                  15

<210> SEQ ID NO 30
<211> LENGTH: 15
<212> TYPE: PRT
<213> ORGANISM: Human papillomavirus type 16

<400> SEQUENCE: 30

Val Tyr Ile Pro Leu Phe Leu Ile His Thr His Ala Arg Phe Leu
1               5                   10                  15

<210> SEQ ID NO 31
<211> LENGTH: 15
<212> TYPE: PRT
<213> ORGANISM: Human papillomavirus type 16

<400> SEQUENCE: 31

Ile Pro Leu Phe Leu Ile His Thr His Ala Arg Phe Leu Ile Thr
1               5                   10                  15
```